(12) United States Patent
Guo et al.

(10) Patent No.: US 9,086,379 B2
(45) Date of Patent: *Jul. 21, 2015

(54) SYSTEM FOR CHEMICAL SEPARATION AND IDENTIFICATION

(75) Inventors: Xun Guo, San Jose, CA (US); Hong Wang, Cupertino, CA (US)

(73) Assignee: OptoTrace (SuZhou) Technologies, Inc., Suzhou (CN)

( * ) Notice: Subject to any disclaimer, the term of this patent is extended or adjusted under 35 U.S.C. 154(b) by 416 days.

This patent is subject to a terminal disclaimer.

(21) Appl. No.: 13/606,455

(22) Filed: Sep. 7, 2012

(65) Prior Publication Data

US 2012/0327408 A1 Dec. 27, 2012

Related U.S. Application Data

(63) Continuation-in-part of application No. 12/848,893, filed on Aug. 2, 2010, now Pat. No. 8,441,631, which is a continuation-in-part of application No. 11/761,453, filed on Jun. 12, 2007, now Pat. No. 7,812,938, and a continuation-in-part of application No. 11/678,053, filed on Feb. 22, 2007, now Pat. No. 7,790,469, said application No. 11/761,453 is a continuation of application No. 10/852,787, filed on May 24, 2004, now Pat. No. 7,384,792.

(51) Int. Cl.
*G01J 3/44* (2006.01)
*G01N 21/65* (2006.01)

(52) U.S. Cl.
CPC ................. *G01N 21/658* (2013.01); *G01J 3/44* (2013.01); *G01J 3/4412* (2013.01)

(58) Field of Classification Search
CPC ............. G01N 21/6428; G01N 21/65–21/658; G01J 3/44; G01J 3/4412; A61K 2300/00; A61K 45/06
USPC ........................................................ 356/301
See application file for complete search history.

(56) References Cited

U.S. PATENT DOCUMENTS

| 4,752,391 | A | 6/1988 | Porsch |
| 4,952,514 | A | 8/1990 | Haddad |
| 5,904,749 | A | 5/1999 | Chen |
| 6,747,735 | B2 | 6/2004 | Chen |
| 6,812,030 | B2 * | 11/2004 | Ozbal et al. ................. 436/50 |
| 6,928,858 | B2 | 8/2005 | Lin |
| 7,195,461 | B2 | 3/2007 | Allington |
| 7,608,818 | B2 | 10/2009 | Miller |
| 2008/0096289 | A1 * | 4/2008 | Zhou et al. ................. 436/532 |
| 2008/0160630 | A1 * | 7/2008 | Liu et al. ................... 436/164 |

(Continued)

*Primary Examiner* — Tarifur Chowdhury
*Assistant Examiner* — Michael P Lapage
(74) *Attorney, Agent, or Firm* — SV Patent Service

(57) ABSTRACT

An integrated chemical separation device includes a chemical separation unit configured to separate a plurality of substances in a sample solution, a mixing chamber configured to receive the plurality of substances in the sample solution at different times, a chemical separation and detection controller, and a multi-channel valve configured to direct the plurality of substances in the sample solution to the mixing chamber under the control of the chemical separation and detection controller. The chemical separation and detection controller can introduce nano particles in the mixing chambers to allow each of the plurality of substances to be adsorbed on the nano particles. A Raman scattering spectrometer unit emits a laser beam to illuminate molecules adsorbed on the surfaces of the nano particles and obtains Raman spectra from the plurality of substances.

20 Claims, 14 Drawing Sheets

(56) References Cited

U.S. PATENT DOCUMENTS

| | | | |
|---|---|---|---|
| 2010/0210029 A1* | 8/2010 | Meinhart et al. | 436/168 |
| 2010/0296086 A1* | 11/2010 | Wang et al. | 356/301 |
| 2012/0077260 A1* | 3/2012 | Sharon et al. | 435/287.2 |
| 2013/0146479 A1* | 6/2013 | Brouwer et al. | 205/780.5 |

* cited by examiner

SECTION A-A

SYSTEM FOR CHEMICAL SEPARATION AND IDENTIFICATION

CROSS-REFERENCE TO RELATED APPLICATIONS

The present patent application is a continuation-in-part application and claims priority to commonly assigned pending U.S. patent application Ser. No. 12/848,893 titled "Integrated device capable of performing chemical separation and light scattering", filed Aug. 2, 2010 by the same inventors. The pending U.S. patent application Ser. No. 12/848,893 is a continuation-in-part application of and claims priority to commonly assigned pending U.S. patent application Ser. No. 11/761,453 titled "Integrated chemical separation light scattering device" filed Jun. 12, 2007, and U.S. patent application Ser. No. 11/678,053 (issued as U.S. Pat. No. 7,812,938) titled "Micro structure for sensing trace chemicals" filed Feb. 22, 2007. U.S. patent application Ser. No. 11/761,453 is a continuation application of and claims priority to U.S. patent application Ser. No. 10/852,787 (issued as U.S. Pat. No. 7,384,792), entitled "Method of fabricating nano-structured surface and configuration of surface enhanced light scattering probe", filed May 24, 2004. The content of the above patent applications are incorporated herein by reference.

BACKGROUND OF THE INVENTION

The present application relates to chemical separation methods and apparatuses.

In many fields, such as environmental monitoring and protection, airport security, food safety, and disease detection and diagnosis, it is often necessary to detect and identify the chemical compositions of an unknown sample. This task is often performed by first separating the different compounds in the sample, and then applying an identification technique to each isolated compound. One of the most popular methods for separating unknown compounds in a gas or liquid phase is called gas chromatography (GC), where the unknown sample is transformed into a carrier gas, if not already in the gaseous state, and the various compounds in the gas are separated due to their differing gaseous properties, such as polarity, affinity to the column and surrounding condition, etc. A standard method for isolating unknown compounds in a liquid phase is called liquid chromatography (LC).

Once the compounds are isolated, they may be identified. The simplest way to identify the compounds is by noting the retention time it takes for each compound to pass through the gas or liquid chromatograph, since different compounds correspond to different retention times to do so. But this method is limited to samples where much is known about the components and need pure standards to get their retention time at the same running conditions.

A more powerful method for identifying isolated compounds examines the intensity of different wavelengths of light emitted, transmitted, reflected, or scattered by the compound. This technique, called spectroscopy, works if each compound emits, transmits, reflects, or scatters light differently and if the spectroscopic instrument has sufficient spectral resolution to detect these differences. More specifically, different chemical compounds emit, transmit, reflect, or scatter different wavelengths of light with differing intensities. A graph or picture of such data is called the spectrum of that compound. Different types of spectroscopy reproduce the spectrum of a compound over different wavelengths and/or under different conditions. If the type of spectroscopy used provides a unique spectrum for each chemical compound, an unknown compound can be identified by producing its spectrum (for example, by illuminating the compound and measuring the light reflected, scattered, or emitted therefrom) and comparing its spectrum with the spectra of known compounds. As a result, gas or liquid chromatographs, which isolate compounds from a sample, are often used with spectrometers, which identify the compounds once they are isolated.

A challenge for gas or liquid chromatography is to provide a flexible and convenient device while still being able to perform the detection of the sample materials. Another challenge for gas or liquid chromatography is to have high sensitivity in the device such that a minute amount of the trace chemicals can be accurately detected.

SUMMARY OF THE INVENTION

In one general aspect, the present invention relates to an integrated chemical separation device that includes a chemical separation unit that can separate a plurality of substances in a sample solution and sequentially output of the plurality of substances in the sample solution; one or more mixing chambers that can receive the plurality of substances in the sample solution at different times; a chemical separation and detection controller; a multi-channel valve that can sequentially direct the plurality of substances in the sample solution to the one or more mixing chambers under the control of the chemical separation and detection controller, wherein the chemical separation and detection controller is that can introduce nano particles in the one or more mixing chambers to allow each of the plurality of substances to be adsorbed on the nano particles; and a Raman scattering spectrometer unit that can emit a laser beam to illuminate molecules adsorbed on the surfaces of the nano particles and to obtain Raman spectra from the plurality of substances.

Implementations of the system may include one or more of the following. The integrated chemical separation device can further include a computer that can identify the plurality of substances from the light scattered from the molecules adsorbed on the nano particles. The integrated chemical separation device can further a chemical detector coupled to the output of the chemical separation unit, wherein the chemical detector can detect the plurality of substances in the sample solution as each of the plurality of substances exits the chemical separation unit and to send a detection signal to the chemical separation and detection controller, wherein the chemical separation and detection controller can switch the multi-channel valve to direct one of the plurality of substances to one of the one or more mixing chambers. The chemical separation and detection controller can control the multi-channel valve to direct adjacent substances of the plurality of substances in the sample solution to different ones of the one or more mixing chambers. The nano particles cab have average diameters ranging from 2 nm to 500 nm. The nano particles can have a size distribution characterized by an average diameter da and a distribution width dw, wherein the ratio dw/da is between about 0.01 and about 3. The nano particles can include a material selected from a group consisting of a metal, a metal alloy, an oxide material, carbon, silicon, a polymeric material, a magnetic or ferromagnetic material, carbon nano tubes, or a combination thereof. The nano particles can include Al, Ag, Au, Cu, Fe, Co, Ni, Cr, Zn, Sn, Pd, or Pt, C, Si, or an oxide thereof, or a combination thereof. The nano particles can be formed in a core-shell structure by two or more materials. The chemical separation and detection controller can introduce a salt solution in the one or more mixing chambers to enhance intensities of the Raman spectra. The salt solution can include multi-valence ions. The salt solution can include $Na^+$, $K^+$, $Li^+$, $Ca^{++}$, $Ba^{++}$, $Sr^{++}$, $Mg^{++}$, $Mn^{++}$, $Al^{+++}$, $Zn^{++}$, $Sn^{++}$, $Sn^{++++}$, $F^-$, $Cl^-$, $Br^-$, or $I^-$. After mixing with the salt solution, the sample solution can have an ionic concentration from about 100 µM to a saturated level. The integrated chemical separation device can further a first container that can hold a nano particle solution comprising the nano particles; and a first valve in fluidic communication with the first container and one of the one or more mixing chambers, wherein the chemical separation and detection controller can control opening and closing of the first valve to control releases of the nano particles into the one or more mixing chambers. The integrated chemical separation device can further a second solution container that can a salt solution; and a second valve in fluidic communication with the second container and the one of the one or more mixing chambers, wherein the chemical separation and detection controller can control opening and closing of the second valve to control releases of the salt solution into the one or more mixing chambers. The chemical separation unit can include a liquid chromatography (LC) column or a high performance liquid chromatography (HPLC) column. The chemical separation and detection controller can control temperature or pressure of the sample solution in the chemical separation unit. The one or more mixing chambers each can include a transparent wall or window to allow transmission of the laser beam and the scattered light. The Raman scattering spectrometer unit can include a laser source that can emit the laser beam to illuminate the molecules adsorbed on the nano particles in one of the one or more mixing chambers and a Raman spectrometer that can produce a Raman spectrum in response to scattered light from the molecules adsorbed on the surfaces of the nano particles.

In another general aspect, the present invention relates to an integrated chemical separation device that includes a single device body; a chemical separation unit that can separate a plurality of substances in a sample solution and sequentially output of the plurality of substances in the sample solution; one or more mixing chambers that can receive the plurality of substances in the sample solution at different times; a chemical separation and detection controller; a multi-channel valve that can sequentially direct the plurality of substances in the sample solution to the one or more mixing chambers under the control of the chemical separation and detection controller, wherein the chemical separation and detection controller is that can introduce nano particles in the one or more mixing chambers to allow each of the plurality of substances to be adsorbed on the nano particles; and a Raman scattering spectrometer unit that can emit a laser beam to illuminate molecules adsorbed on the surfaces of the nano particles and to obtain Raman spectra from the plurality of substances, wherein the chemical separation unit, the one or more mixing chambers, the multi-channel valves, the chemical separation and detection controller, and the Raman scattering spectrometer unit are held in or mounted to the single device body.

In another aspect, the present invention relates to an integrated chemical separation device that includes a single device body, a chemical separation unit that can separate a chemical from a fluid, a Raman sensor substrate comprising a plurality of nano rods on the Raman sensor substrate or nano holes in the Raman sensor substrate, wherein the surfaces of the nano rods or nano holes comprise a metallic material that can adsorb molecules of the chemical from the fluid; and a Raman scattering spectrometer unit that can emit a laser beam to illuminate the molecules adsorbed on the surfaces of the plurality of nano rods or nano holes in the Raman sensor substrate and to detect the chemical from the light scattered from the molecules adsorbed on the surfaces of the plurality of nano rods or nano holes in the Raman sensor substrate, wherein the chemical separation unit, the Raman sensor substrate, and the Raman scattering spectrometer unit are held in or mounted to the single device body.

Implementations of the system may include one or more of the following. The metallic material can include a noble metal. The Raman sensor substrate can include: a silicon or a glass based substrate; and a conductive layer on the silicon based substrate, wherein the nano rods are positioned standing on the conductive layer. The conductive layer can include titanium or nickel. The plurality of nano rods can have diameters in the range from 1 nanometer to 300 nanometers. The plurality of nano rods can have heights in the range from 1 nanometer to 1000 nanometers. The plurality of nano holes can have diameters in the range from 1 nanometers to 300 nanometers. The plurality of nano holes can have depths in the range from 1 nanometer to 1000 nanometers. The plurality of nano rods or nano holes in the Raman sensor substrate can have center-to-center spacing in the range from 1 nanometer to 1000 nanometers. The chemical separation unit can separate the chemical from a gas. The chemical separation unit can include one a capillary column or a molecular sieve, each of which being configured to separate the chemical from a gas or a liquid. The integrated chemical separation device can further include an injector that can inject the gas or liquid into the capillary column. The chemical separation unit can separate the chemical from a gas or a liquid. The chemical separation unit can include a separation liquid chromatography (LC), or gas chromatography (GC), column or a molecular sieve, each of which being configured to separate the chemical from the liquid or gas. The integrated chemical separation device can further include a first pump that can pump a liquid or a gas through the chemical separation unit and to the Raman sensor substrate. The integrated chemical separation device can further include a second pump that can pump an effluent liquid or gas away from the Raman sensor substrate or test reagent and out of the integrated chemical separation device; and a solvent reservoir that can provide a solvent to merge with the effluent liquid or gas to be pumped out of the integrated chemical separation device. The Raman sensor substrate can include a fluid conduit that can transport a liquid to the vicinity of the surfaces of the plurality of nano rods or nano holes, or the test reagent, to allow the molecules of the chemical to adsorb to the surfaces of the nano rods or nano holes, or nano particles in a test reagent. The integrated chemical separation device can further include a sensor controller that can produce a temperature bias, an electric field, or a magnetic field to the Raman sensor substrate, or test reagent, to assist adsorption of molecules of the chemical from the fluid on the surfaces of the nano rods or nano holes, or in the test reagent. The integrated chemical separation device can further include a chemical separation controller that can control the chemical separation unit to separate of the chemical from the fluid. The chemical separation controller can control temperature or a pressure of the fluid in the chemical separation unit to assist the separation of the chemical from the fluid. The Raman scattering spectrometer unit can include a laser source that can emit the laser beam to illuminate the molecules adsorbed on the surfaces of the plurality of nano rods or nano holes in the Raman sensor substrate, or of the nano particles in a test reagent; and a Raman spectrometer that can produce a Raman spectrum in response to scattered light from the molecules adsorbed on the surfaces of the plurality of nano rods or nano holes in the Raman sensor substrate, or of the nano particles in a test reagent. The integrated chemical separation device can further include a sensor controller that can control the temperature or to apply an electric field or a magnetic field to the Raman sensor substrate to assist adsorption of molecules of the chemical from the fluid on the surfaces of the nano rods or nano holes; a chemical separation controller that can control temperature or pressure of the fluid in the chemical separation unit; and a computer processor that can control the sensor controller, or the chemical separation controller, or both the sensor controller and the chemical separation controller, wherein the sensor controller, the chemical separation controller, and the computer processor are held in or mounted to the single device body.

In another aspect, the present invention relates to integrated chemical separation device that includes a single device body; a chemical separation unit that can separate a chemical from a fluid; a Raman sensor substrate comprising a plurality of nano particles on the Raman sensor substrate a test reagent containing nano particles, wherein the surfaces of the nano particles can adsorb molecules of the chemical from the fluid; and a Raman scattering spectrometer unit that can emit a laser beam to illuminate the molecules adsorbed on the surfaces of the plurality of nano particles on the Raman sensor substrate and to detect the chemical from the light scattered from the molecules adsorbed on the plurality of nano particles on the Raman sensor substrate, wherein the chemical separation unit, the Raman sensor substrate, and the Raman scattering spectrometer unit are held in or mounted to the single device body.

Implementations of the system may include one or more of the following. The nano particles can be deposited on the surface of the Raman sensor substrate by introducing a solution on the surface followed by evaporation of the solvent in the solution. The nano particles can include a material selected from a group consisting of a metal, a metal alloy, an oxide material, silicon, a polymeric material, a magnetic or ferromagnetic material, and a combination thereof. The nano particles can include a material selected from a group consisting of Al, Ag, Au, Cu, Fe, Co, Ni, Cr, Zn, Sn, Pd, Pt, Si, and its metal oxide, a combination thereof, or a combination of multi-layer or multi-shell structured nano particles thereof. The nano particles can include carbon nano tubes. The nano particles can be in sol gel liquid phase.

In another aspect, the present invention relates to method for separating a substance from a fluid and for determining the identity of the substance. The method includes separating a substance from a fluid using a substance separation unit in an integrated substance separation and analysis device; adsorbing molecules of the substance from the fluid to a metallic material on the surfaces of nano rods, nano holes, or nano particles in a Raman sensor substrate mounted in the integrated chemical separation and analysis device, in in a test reagent; emitting a laser beam by a Raman scattering spectrometer unit in the integrated chemical separation and analysis device to illuminate the molecules adsorbed on the surfaces of the plurality of nano rods, nano holes, or nano particles in the Raman sensor substrate or in a test reagent, and determining the identity of the substance from the light scattered from the molecules adsorbed on the surfaces of the plurality of nano rods, nano holes, in the Raman sensor substrate, or nano particles the test reagent.

Implementations of the system may include one or more of the following. The Raman scattering spectrometer unit can include a laser source that can emit the laser beam to illuminate the molecules adsorbed on the surfaces of the plurality of nano rods or nano holes in the Raman sensor substrate, or nano particles in test reagent; and a Raman spectrometer that can produce a Raman spectrum in response to scattered light from the molecules adsorbed on the surfaces of the plurality of nano rods or nano holes on the Raman sensor substrate, or nano particles in the test reagent. The method can further include controlling the temperature or to apply an electric field or a magnetic field by a sensor controller to the Raman sensor substrate or test reagent to assist adsorption of molecules onto the surface of nano rod or nano holes of the sensor substance, or nano particles in a test reagent, from the fluid. The step of separating a substance from a fluid can include controlling the temperature or the pressure of the fluid in the chemical separation unit. The method can further include introducing a solution or a sol gel comprising the nano particles onto the surface of a substrate; and allowing the solvent in the solution or sol gel to evaporate before the molecules of the substance are adsorbed to the surfaces of the nano particles. The fluid can be a gas, or a liquid, wherein the molecules of the substance in the gas, or the liquid, are introduced to the on the surfaces of nano rods, nano holes, or nano particles in the test reagent.

Embodiments may include one or more of the following advantages. The disclosed system and methods provide an integrated device that can perform chemical separation and Raman scattering to detect and analyze trace amount of chemicals. The disclosed integrated device can significantly enhance detection sensitivity by using replaceable Raman sensor substrate or test reagent having nanometer-scale structures and associated surfaces that can adsorb the molecules of the chemical to be detected. The detection sensitivity can also be increased by optimizing the directions of incident laser beam and the scattered laser light relative to the orientations of the nanometer-scale structures in the Raman sensor substrate or test reagent.

The disclosed system and methods also provide a compact and integrated chemical separation and Raman scattering device with reduced number of components, decreased footprint, and thus reduced system costs. The integrated chemical separation and Raman scattering device can be easily transported and deployed at locations convenient for sample collection, which allows fast measurement turn around. The disclosed systems and methods can also be flexibly applied to or combine with a variety of chemical separation technologies such as liquid chromatography (LC), high performance liquid chromatography (HPLC), and gas chromatography (GC), etc.

Details of one or more embodiments are set forth in the accompanying drawing and in the description below. Other features, objects, and advantages of the invention will become apparent from the description and drawings, and from the claims.

DETAILED DESCRIPTION OF THE INVENTION

Figure 1A:
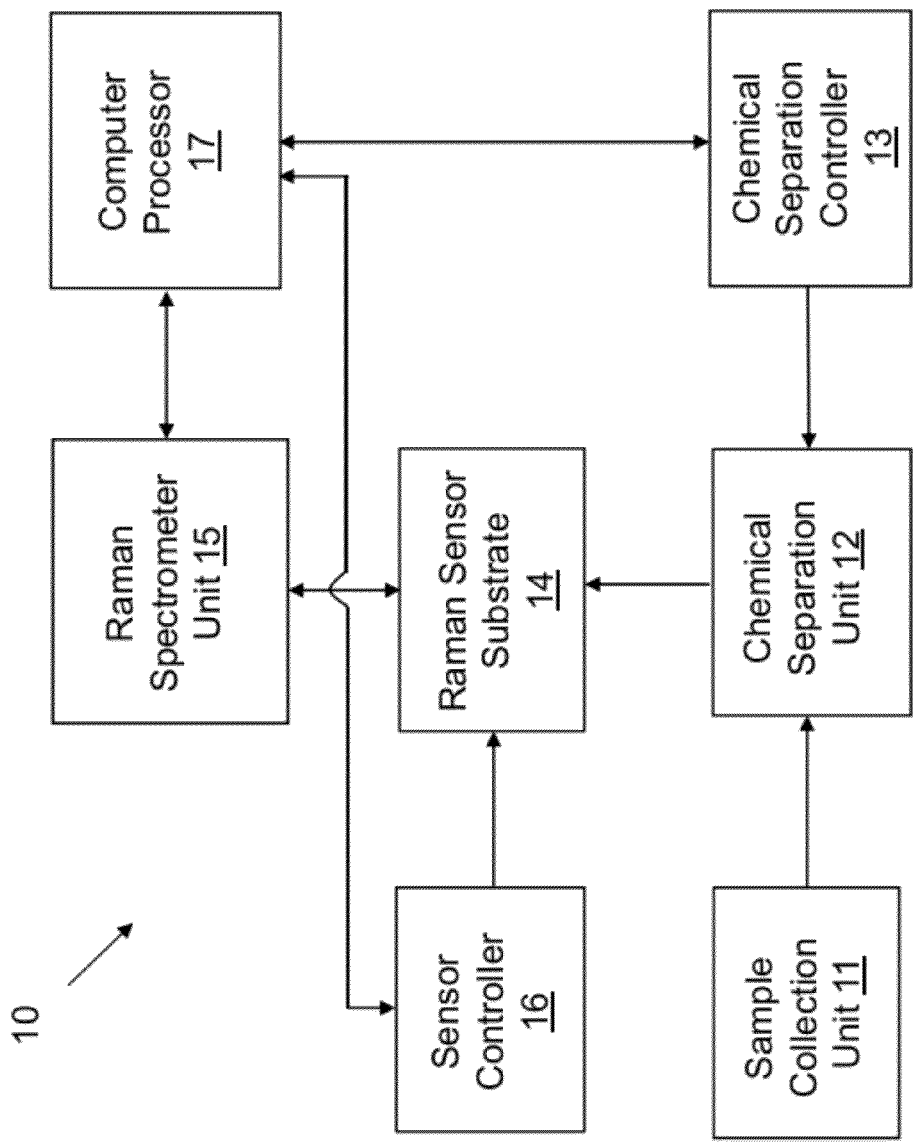
FIG. 1A is a system block diagram of an integrated Raman scattering chemical separation device in accordance to present invention.

An integrated Raman scattering chemical separation device 10, referring to FIG. 1A, can include a sample collection unit 11, a chemical separation unit 12, a chemical separation controller 13, a Raman sensor substrate or test reagent 14, a Raman spectrometer unit 15, and a sensor controller 16, which can be contained in or held by a device body as shown in the examples described below. The device body can include a rigid chassis, a chamber, a rigid fixture or frame that can define an enclosure. The sample collection unit 11 can collect samples from a gas, a liquid, a solid, or an aerosol. The sample may contain trace chemical that is to be detected and identified by the integrated Raman scattering chemical separation device 10. The chemical separation unit 12 can separate the one or more chemicals contained in the sample under the control of the chemical separation controller 13. As describe in more detail below, the chemical separation controller 13 can control the pressure and the temperature of the fluid (a liquid or a gas) or the aerosol in the chemical separation unit 12 to produce more distinct separation of the chemicals. A chemical separated by the chemical separation unit 12 is received by the Raman sensor substrate or test reagent 14.

Figure 1B:
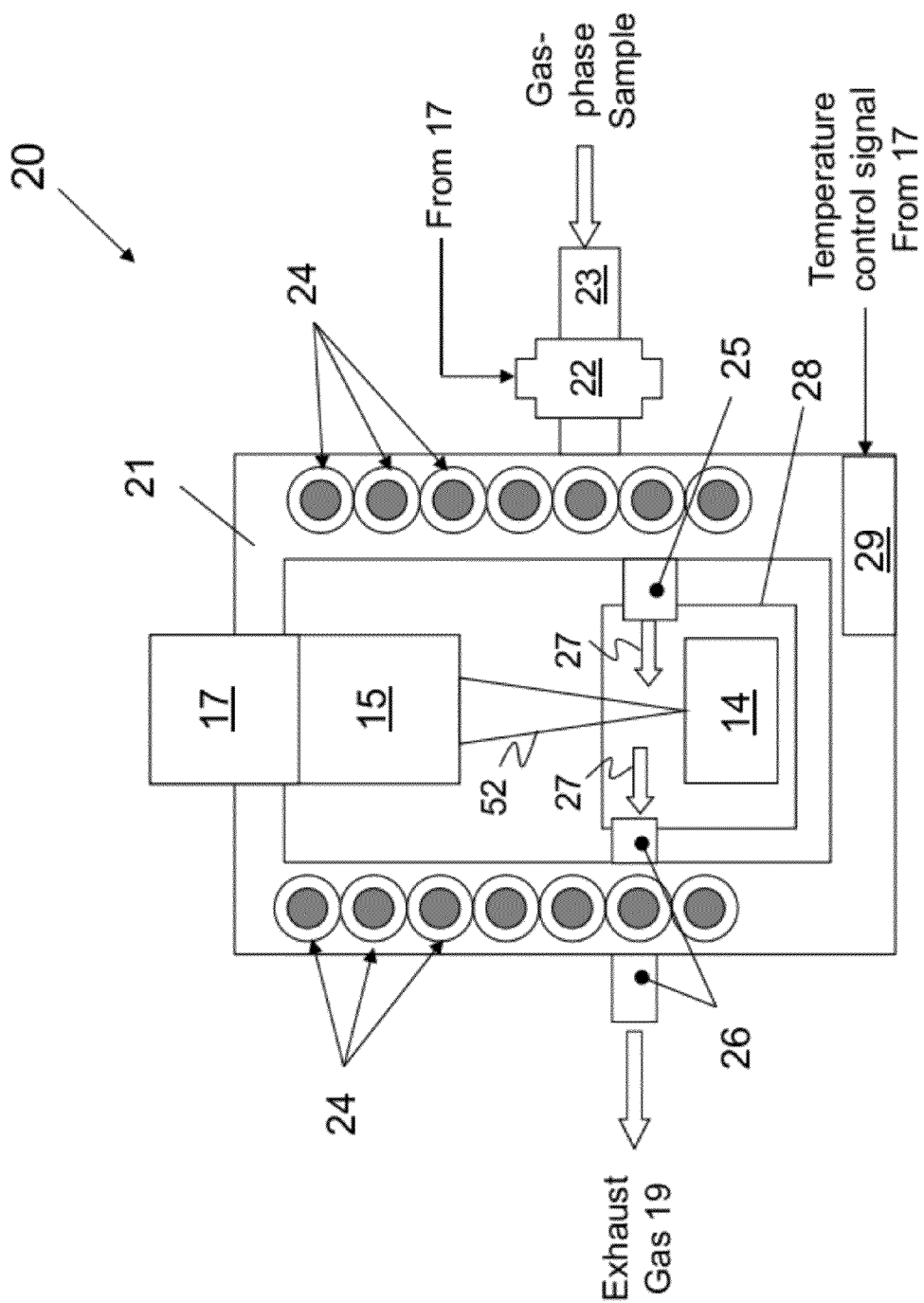
FIG. 1B is a schematic diagram of an exemplified integrated Raman scattering gas chemical separation device.
Figure 1C:
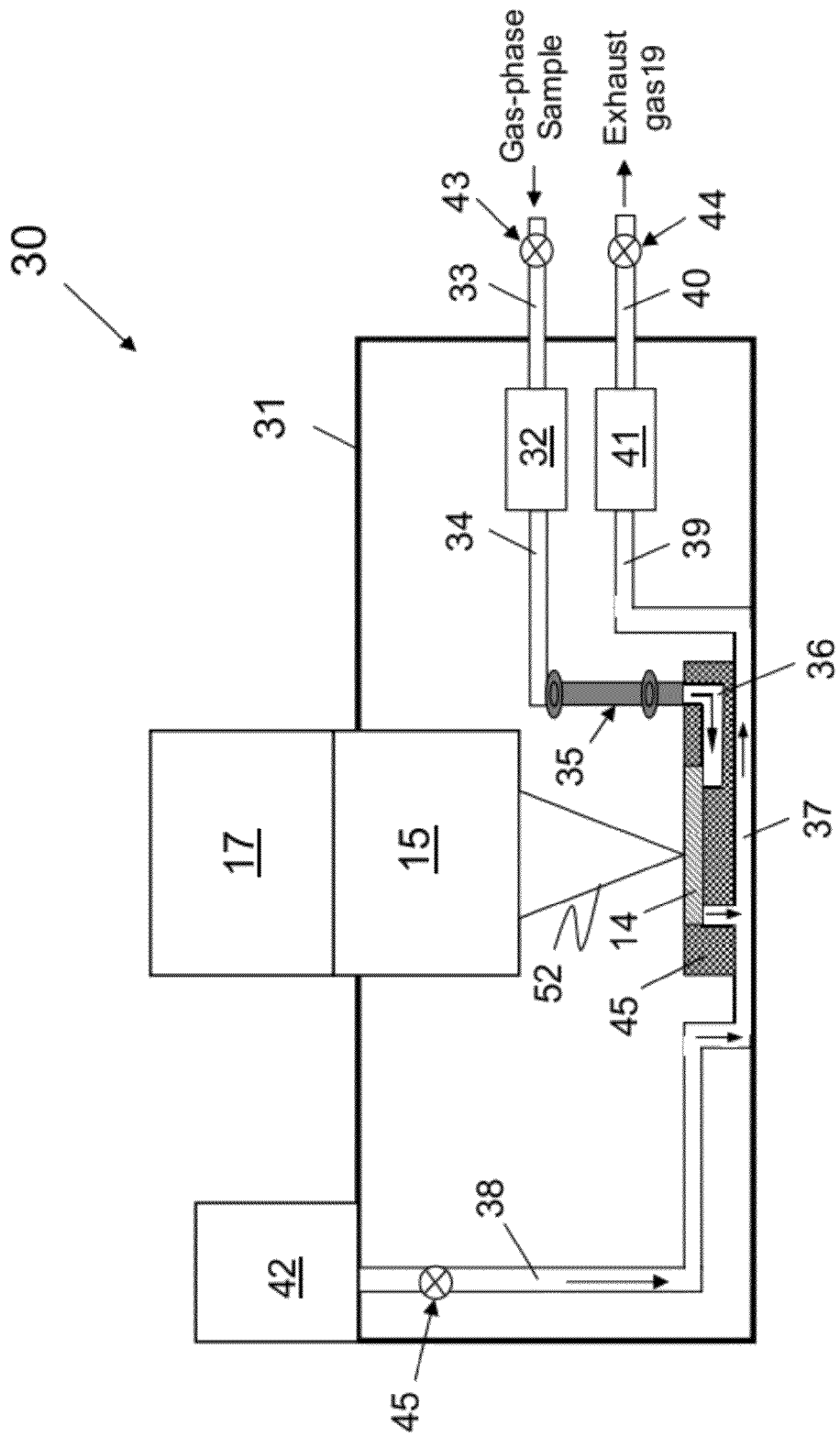
FIG. 1C is a schematic diagram of an exemplified integrated Raman scattering liquid chemical separation device.
Figure 1D:
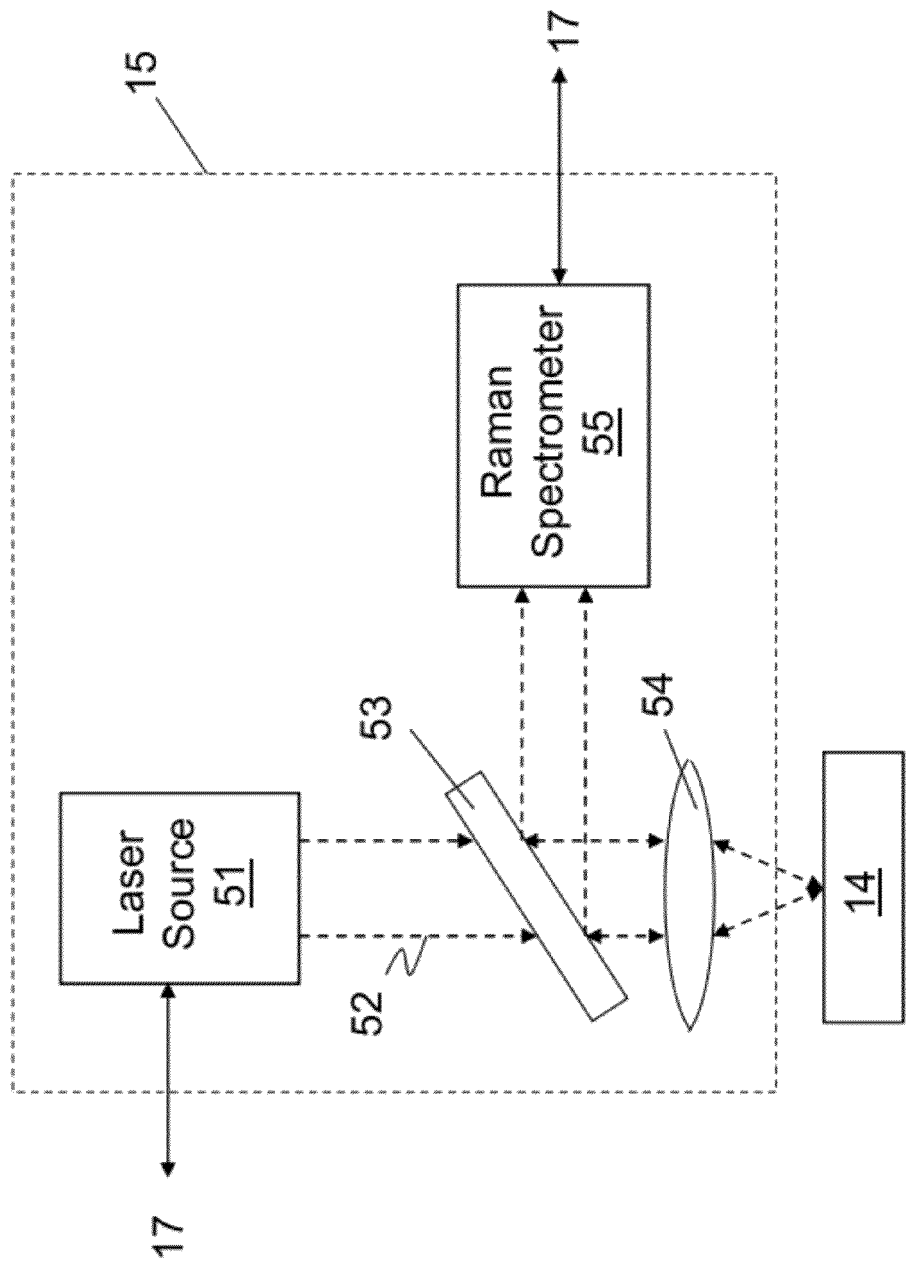
FIG. 1D is a schematic diagram of an exemplified integrated Raman spectrometer unit compatible with the exemplified integrated Raman scattering gas chemical separation device of FIG. 1B and the exemplified integrated Raman scattering liquid chemical separation device of FIG. 1C.

The Raman sensor substrate or test reagent 14 can include microscopic or nano structures such as an array of rods on a substrate or an array of holes in a substrate, or nano particles in a test reagent. The diameters of the rods or the holes can be in the range from 0.5 to 1000 nanometers. The chemical received by the Raman sensor substrate or test reagent 14 can be adsorbed by the surfaces of the microscopic or nano structures. As shown in FIGS. 1B-1D, the Raman spectrometer unit 15 can include a laser source 51 that can emit a laser beam 52. The laser beam 52 can pass a beam splitter 53 and an optical system 54 to illuminate the Raman sensor substrate or test reagent 14. Light scattered from the Raman sensor substrate or test reagent 14 can be collected by the optical system 54 and directed to a Raman spectrometer 55 by the beam splitter 53. A Raman spectrum of the chemical adsorbed on the surfaces of the microscopic or nano structures on the Raman sensor substrate or test reagent 14 can be obtained by the Raman spectrometer 55. The Raman spectrometer 55 and the laser source 51 can be controlled by the computer processor 17.

Referring back to FIG. 1A, the Raman spectrum can be analyzed by a computer processor 17, wherein the chemical can be determined by identifying one or more signatures of the chemical in the Raman spectrum. The computer processor 17 can also be held in the same device body. The chemical separation controller and the sensor controller 16 can be controlled by the computer processor 17. The laser source 51 can also be controlled by the computer processor 17. The Raman spectrometer 55 can be controlled by the computer processor 17 and send measured Raman spectral data to the computer processor 17 for analyses and the determination of the chemical.

The surface of the micro structure structures can include a conductive material, which can enhance the signal strength of the Raman spectroscopy. The strength of the Raman scattering signal can be further enhanced by controlling the temperature of the substrate, or apply an electric field or a magnetic field to the substrate by a sensor controller 16. The Raman sensor substrate can include a plurality of holes having diameters in the range from 0.5 to 1000 nanometers. The Raman sensor substrate can include a plurality of rods or holes having center to center spacing in the range from 0.5 to 1000 nanometers, and height or depth of rods or holes in the range from 0.5 nanometers to 1000 nanometers. Details about the structures and the operations of the Raman sensor substrate or test reagent 14 and the sensor controller 16 are disclosed in the above referenced and commonly assigned U.S. patent application Ser. No. 10/852,787 (Issued as U.S. Pat. No. 7,384,792), entitled "Method of fabricating nanostructured surface and configuration of surface-enhanced light scattering probe", filed May 24, 2004, and U.S. patent application Ser. No. 11/562,409 (issued as U.S. Pat. No. 7,460,224), entitled "Arrays of nano structures for surface-enhanced Raman scattering", filed Nov. 21, 2006, and U.S. patent application Ser. No. 12/403,522 (issued as U.S. Pat. No. 8,102,525), entitled "Improved systems and methods for detecting chemicals and biological substances", filed Mar. 13, 2009, the content of which is incorporated herein by reference.

In an exemplified implementation, referring to FIG. 1B, an integrated Raman scattering gas chemical separation device 20 can include a device body 21, an injector 22 and an inlet 23 mounted on the device body 21, one or more capillary columns 24 in fluid connection with the injector 22, a gas chamber 28, and an inlet 25 and an outlet 26 connecting the gas chamber 28 and the exterior of the device body 21. The device body 21 can be a rigid chassis, a rigid frame, or a rigid cylinder that can hold the capillary columns 24, the gas chamber 28, the injector 22 and the inlet 23, and the inlet 25 and the outlet 26. The device body 21 can be formed of metal, glass, or other rigid materials, or a combination of different types of rigid materials. The capillary columns 24 can be made of stainless steel, Teflon, a plastic material, and silicon glass. Different materials can be selected depending on the chemical to be detected. The ends of the capillary columns 24 can be screw-in mountable to the inlet 25 and the injector 22. The injector 22 can inject the gas into the capillary columns 24 and provide pressure difference to push the gas flowing through the capillary columns 24.

The Raman sensor substrate 14 can be held inside the gas chamber. The gas chamber 28 can be made of stainless steel that can enclose the gas samples to a desirable concentration to allow the chemicals to be adsorbed on the microscopic or nano surfaces of the Raman sensor substrate 14. The gas chamber 28 can include a window that allows optical communications between a Raman spectrometer unit 15 and the Raman sensor substrate 14. The Raman spectrometer unit 15 can be held inside or on the device body 21. The integrated Raman scattering gas chemical separation device 20 can further include a temperature controller 29 that is in thermal communication with the capillary columns 24. A computer processor 17 can also be included in the integrated Raman scattering gas chemical separation device 20. The computer processor 17 can also be held inside or on the device body 21. The computer processor 17 can generate the temperature control signal and analyze the Raman spectral signals output from the Raman spectrometer 55 in the Raman spectrometer unit 15. The integrated Raman scattering gas chemical separation device 20 can be built in compact dimensions compared to a collection of conventional gas chemical separation systems and Raman scattering spectroscopy systems. For example, the disclosed integrated Raman scattering gas chemical separation device 20 can have a compact footprint of, for example, approximately 100 cm by 80 cm, and a height of 100 cm. In another example, the device body 21 of the integrated Raman scattering gas chemical separation device can have dimensions of 4"×6"×4" (Width×Length×Height).

Because of its compact dimensions, the integrated Raman scattering gas chemical separation device 20 can be easily transported and placed at a location that is easy for gas sample collection. For example, the integrated Raman scattering gas chemical separation device 20 can be placed next to a security check point at an airport or seaport for detecting harmful materials such as explosives, chemical or biological agents, toxins, nuclear materials, and flammable materials. A gas phase sample can be collected by an injector 22 through the inlet 23. The injector 22 can include an air pump that can draw the gas-phase sample from the ambient environment under the control of the computer processor 17. The gas-phase sample collected is pressure fed into the capillary columns 24. The pressure applied to the flowing gas sample and thus the average speed of the gas molecules can be controlled by the computer processor 17. The gas-phase sample can include a mixture of chemicals each having different molecular properties. The capillary columns 24 can produce different amounts of frictions on the flow of the different species of molecules such that they can be separated through the length of the capillary columns 24 to produce phase separated gas 27. For example, lighter weight gas molecules tend to move faster than heavier molecules. The absorption to the side walls of the capillary columns 24 can also affect the mobility of the gas molecules. The fast moving gas phase molecules can exit the capillary columns 24 and enter the gas chamber 28 first, followed by the slow moving molecules. The molecules in the phase separated gas 27 can be adsorbed to the micro-structured surfaces on the Raman sensor substrate 14. The Raman spectrometer unit 15 can measure the Raman spectrum of the adsorbed molecules at the micro-structured surfaces on the Raman sensor substrate 14. The Raman spectra are measured at different times as different molecules enter the gas chamber 28 and become adsorbed by the micro-structured surfaces on the Raman sensor substrate 14. The exhaust gas 19 exits the outlet 26.

In one implementation, a same Raman sensor substrate 14 can be used to adsorb different molecules from the gas phase. The late coming molecules can at least partially replace some of the earlier adsorbed molecules on the micro-structured surfaces on the Raman sensor substrate 14. Alternatively, Raman sensor substrate 14 can be replaced over time to provide fresh microscopic or nano-structured surfaces to adsorb molecules as new species of molecules enter the gas chamber 28.

In one implementation, the temperature of the capillary columns 24 can be controlled by the temperature controller 29 to enhance the separation of the molecules. For example, the temperature of the capillary columns 24 can be controlled at a relatively high temperature at the initial stage of the gas-phase separation to accelerate the movement of the fast moving gas molecules. The temperature of the capillary columns 24 can be decreased over time to slow down the slow moving gas-phase molecules. The temperature gradient can thus lengthen the time separation between the fast moving and slow moving molecules, which can increase collection time for the spectral data, and thus increase signal-to-noise ratio in the Raman spectra.

In another exemplified implementation, referring to FIG. 1C, an integrated Raman scattering liquid chemical separation device 30 can include a device body 31, an inlet 33 mounted on the device body 31, a fluidic pump 32, a separation LC column 35 in fluid connection with the fluidic pump 32 via a feed line 34, a substrate 45 having fluid conduits 36-37, a fluidic pump 41 in fluidic connection with the fluid conduit 37 via the return line 39, and an outlet 40 mounted on the device body 31 and in fluidic communication with the fluidic pump 41. The fluid conduits 36-37 are connected with a Raman sensor substrate or a test reagent 14 and can bring a fluid or an aerosol to the vicinity of the microscopic or nano surfaces of the Raman sensor substrate or test reagent 14. The separation LC column 35 can for example be implemented by the capillary columns 24 (FIG. 1B). The device body 31 is a rigid enclosure that can contain, hold, or be mounted with the various components described above. For example, the device body can be a chassis, a cabinet, or a chamber that is made of one or more rigid materials.

The Raman scattering liquid chemical separation device 30 can also include a solvent reservoir 42 that can provide solvent through feed line 38 to the fluid conduit 37, and one or more valves 43-45 for opening or closing the fluid flow through the conduits and the pumps. The Raman scattering liquid chemical separation device 30 can also include a Raman spectrometer unit 15 and a computer processor 17. The computer processor 17 can control the fluidic pumps 32 and 41, and optionally the valves 43-45. The substrate 45 can be mounted at the bottom of the device body 31. The feed line 38, the inlet 33, the outlet 40, and the Raman spectrometer unit 15 can be mounted on the device body 31. The integrated Raman scattering liquid chemical separation device 30 can be configured as a compact single piece of equipment that can easily be transported to a deployment location.

In operation, valves 43-45 are opened. A liquid containing a mixture of chemicals can be pumped by the fluidic pump 32 to the separation LC column 35 via the feed line 34. The separation LC column 35 can separate the chemical compounds to cause the different types of molecules to flow out of the separation LC column 35 at different times, called retention time for each chemical, into the fluid conduit 36. The fluid carrying separated molecules are transported to the microscopic or nano surfaces of the Raman sensor substrate or a test reagent 14, wherein the molecules can adsorb to the microscopic or nano surfaces. As described above, the Raman sensor substrate or test reagent 14 can include structures such as holes or rods, or nano particles in a test reagent, in diameters in the range from a nanometer to a few hundred nanometers. The surfaces of the structures can be coated with material that has high affinity to the molecules to be detected. The effluent fluid exits the Raman sensor substrate, or a channel line which chemicals under test and test reagent containing nano particles, 14 and flows into the fluid conduit 37 and the return line 39, and is finally pumped out of outlet 40 by the fluidic pump 41. The solvent reservoir 42 can provide solvent to the fluid conduit 37 and the return line 39 to balance the flow rate and pressure distribution produced by the fluidic pumps 32 and 41.

In some embodiments, the Raman scattering gas chemical separation device 20 or the Raman scattering liquid chemical separation device 30 can include a sensor controller 16 (FIG. 1A) that can a temperature bias, an electric field, or a magnetic field to the Raman sensor substrate or test reagent 14. For example, the sensor controller 16 can apply cooling to the Raman sensor substrate or test reagent 14 can enhance the adsorption of molecules to the microscopic or nano surfaces and thus enhance the Raman spectral signals. The cooling is especially important considering the heating created at the micro structures by the laser beam 52 emitted by the laser source 51. The sensor controller 16 can be controlled by the computer processor 17. The integrated Raman scattering liquid chemical separation device can be made compact. For example, the device body 31 of the integrated Raman scattering liquid chemical separation device can have compact dimensions of, for example, 6"×8"×6" (Width×Length×Height).

Embodiments may include one or more of the following advantages. The disclosed system and methods provide an integrated device that can perform chemical separation and Raman scattering to detect and analyze trace amount of chemicals. The disclosed integrated device can significantly enhance detection sensitivity by using replaceable Raman sensor substrate having nanometer-scale structures and associated surfaces that can adsorb the molecules of the chemical to be detected, or a test reagent containing nano particles. The detection sensitivity can also be increased by optimizing the directions of the polarized incident laser beam and the scattered laser light relative to the orientations of the nanometer-scale structures in the Raman sensor substrate, or applying laser incident configuration structure with larger solid angle to receive more scattered signal.

The disclosed system and methods also provide a compact and integrated chemical separation and Raman scattering device with reduced number of components, decreased footprint, and thus reduced system costs. The integrated chemical separation and Raman scattering device can be easily transported and deployed at locations convenient for sample collection, which allows on-site inspection with fast measurement turn around.

The disclosed systems and methods can also be flexibly applied to a variety of chemical separation technologies such as high performance liquid chromatography (HPLC), gas chromatography (GC), and ion chromatography, etc. In another example, the disclosed system and methods is compatible with chemical separation using molecular sieves. Molecular sieves typical have molecular structures that can trap analyte chemicals to allow unwanted other chemicals to be separated. For example, a molecular sieve material is Zeolite that includes holes for trapping target chemicals from a gas or a liquid. Specifically, nano particles made of polymers, metal beads, chemical beads, and other synthetic compounds can be arranged to be at the surfaces of the sieve holes. The nano particles can be engineered to enhance the trapping of the analyte chemicals and enhance Raman scattering signals. The molecular sieves can be used to separate chemicals from a liquid or a gas in the disclosed integrated Raman scattering liquid chemical separation device or integrated Raman scattering gas chemical separation device.

It is understood that the disclosed system and methods are compatible with different types of chemical separation techniques in addition to LC, HPLC, GC, and IC. The disclosed system and methods are compatible with different types of chemical separation techniques. The computer processor can include wired or wireless communication devices to allow the Raman scattering fluid chemical separation devices to communicate with remote computers or to be controlled by remote computers. Chemicals can thus be monitored and detected by remote Raman scattering fluid chemical separation devices and measurement results fed to a computer in real time. The optical system can exist in different arrangements to facilitate the laser illumination and scattered light collection.

It should be noted that conventional methods of detect chemicals involve chemical separation method first followed by a detector, for example, a UV sensor, or a mass spectroscopy. The presently disclosed systems and methods on nano surface enhanced Raman detection method can be applied with chemical separation method (LC, HPLC, GC, or IC). In the presently disclosed systems and methods, the Raman spectral detection can be integrated with the chemical separation in a single system.

Figure 2:
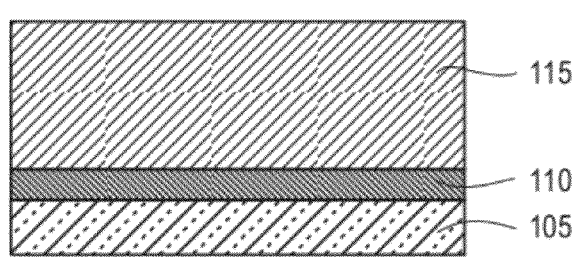
FIG. 2 is a cross-sectional view of a multi-layer structure configured to be used for fabricating a nano-structured surface.

Details about the fabrication of the nano structures in the Raman sensor substrate 14 are described as follows. The Raman sensor substrate 14 can include surface nano structure and top sensing layer. In some embodiments, FIGS. 2 to 6 show the structures at different steps in a process for fabricating nano structures (nano rods or nano holes) compatible with the presently disclosed integrated Raman scattering chemical separation device. FIG. 2 shows a two-layer structure with a silicon substrate 105 (e.g. an n-type silicon wafer or oxidized p-type silicon wafer) and an electrically and thermally conductive layer 110 deposited on a silicon substrate 105. The conductive layer 110 can be formed by metallic materials such as Ti and Ni. The conductive layer 110 can perform several functions: it can provide best adhesion to a subsequently deposited noble metal material, such as Ag or Au. The conductive layer 110 can also apply electrical bias to sensing surface in field application, or as a thermal conductive layer for applying lower temperature of sensing surface. The thickness of this metal film can be controlled in the range of 100 Å-10 μm.

Figure 2B:
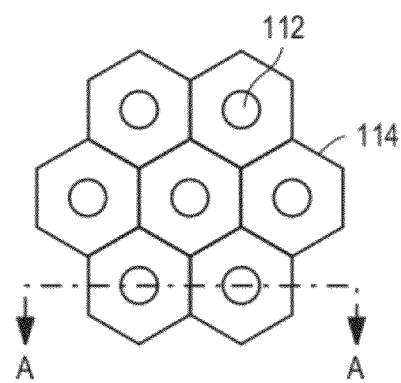
FIG. 2B is a top view of the multi-layer structure of FIG. 2A.
Figure 2A:
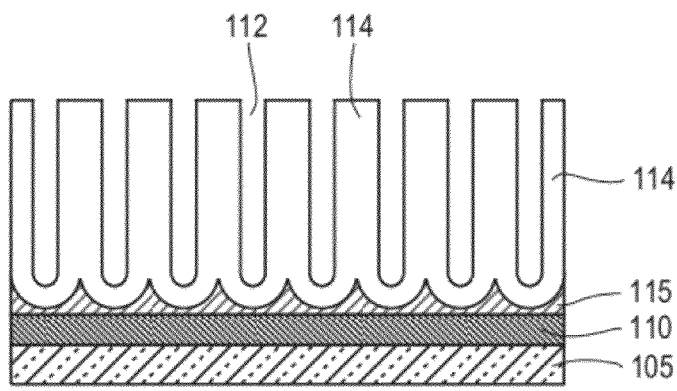
FIG. 2A is a front cross-sectional view of the multi-layer structure of FIG. 2 after anodization.
Figure 2C:
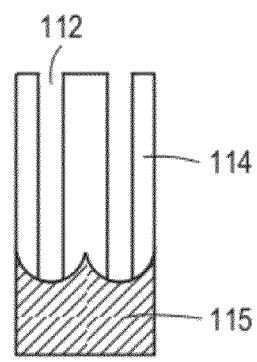
FIG. 2C is a side cross-sectional view along a horizontal line in FIG. 2B.

An aluminum layer 115 is deposited on top of the conductive layer 110. The aluminum layer 115 can have a purity of 99.999% in Al, and a thickness in the range of 1.0-10.0 μm. Prior to anodization, silicon wafers with Ti conductive layer and Al layer are annealed at 400° C.-500° C. in a $N_2$ purged furnace for 2-5 hours to recrystallize the aluminum layer 115. An anodization process is performed to change the aluminum layer 115 to a porous structure comprising aluminum oxide as shown in FIGS. 2A-2C. The porous structure includes a plurality of pores 112 surrounded by pore wall 114. Then wet oxide etch is carried out in FIG. 3 to remove the aluminum oxide in the porous structure. A second anodization process is carried out to consume all aluminum material above the conductive layer 110.

Figure 4:
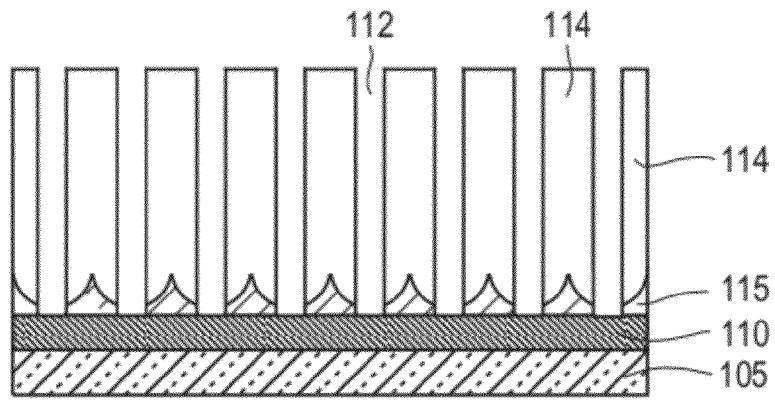
FIG. 4 is a cross-sectional view of the nano-structure surface after the etching down to the conducting layer.

Oxide etching is then carried out to widen the pore diameter, as shown in FIG. 4. After the completion of the wet etch process, the pores 112 are extended downward to reach the conductive layer. The thickness of the resulted porous oxide layer can be controlled by processing parameters of aluminum physical vapor deposition (PVD); anodization and the subsequent wet etch processes. The nano pores can self-assemble to form a hexagonal array. The pore diameter (d) depends on applied anodization voltage (V), current density (i) and electrolyte, and the subsequent pore widening wet etch process, while the inter-pore distance (D) depends on applied anodization V, i and electrolyte.

Figure 5A:
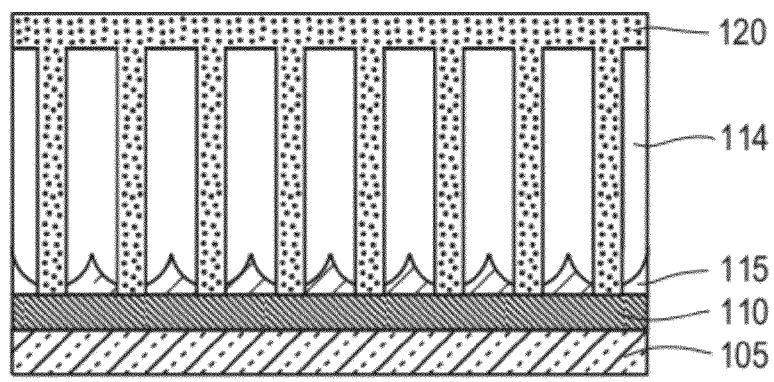
FIG. 5A shows the deposition of a noble metal in the nano holes and on the nano surface structure.

A noble metal 120, with a layer thickness in the range of 1 nm-500 nm, such as 3 nm-200 nm, is introduced in the pores 112, as shown in FIG. 5A. The noble metal 120 can include Ag or Au. The noble metal 120 can be deposited by PVD, ALD, or formed by electroplating or a wet chemical process.

Figure 5B:
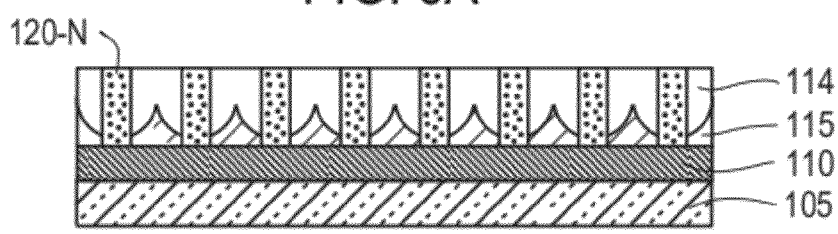
FIG. 5B shows the nano structure after the removal of the noble metal material on the nano structure.
Figure 6:
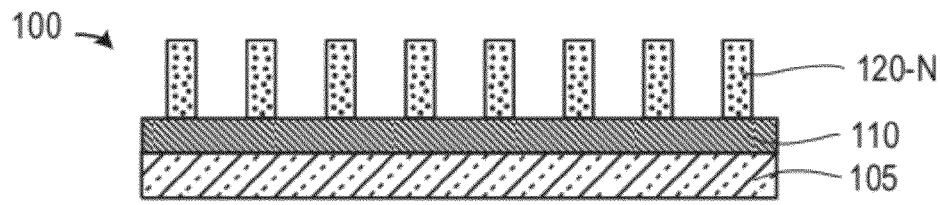
FIG. 6 is a front cross-sectional view of the nano rods formed by the noble metal material after the removal of the oxide material.

The top layer of the noble metal 120 is removed with the noble metal 120-N filled the pores 112, as shown in FIG. 5B. Wet metal etch or CMP is then carried out to planarize the top surface and adjust the heights of the noble metal 120-N filled in the pores 112. The aluminum oxide and the residue aluminum layer 115 between the nano rods 120-N are removed, as shown in FIG. 6, which result in a nano structure 100 comprising an array of nano rods 120-N formed by noble metal material. The nano rods can have controlled height (H) and a well-defined distance (D) between the adjacent nano rods. The dimensions of the nano structure 100 can be controlled and customized using processing parameters in the physical vapor deposition of the aluminum layer, the anodization of the aluminum material, and wet etch and/or chemical-mechanical polishing (CMP) of the anodized structure.

The present invention thus provides a nano-structured surface fabricated by these novel processing steps on a silicon (100) substrate. By using the nano-structured surface, a Raman scattering band around 520 $cm^{-1}$ from silicon substrate is applied as the internal reference for calibrating spectrum frequency and intensity in the field application. A voltage may be applied to the nano-structure sensing surface through the conductive layer 110 for the purpose of attracting electrically charged trace chemical in the form of electrically charged molecular clusters, e.g., either negatively or positively charged particles depending on the sensing applications. Furthermore, the conductive layer 110 can also be cooled to a lower temperature below a normal room temperature to further enhance surface adsorption of molecules of interest.

Figure 7A:
FIGS. 7A-7D are front cross-sectional views of nano structures formed by an alternate process.

In some embodiments, referring to FIGS. 7A to 7F, another process is shown for fabricating a nano structure compatible with the present invention. FIG. 7A shows a two-layer structure comprising an electrically and thermally conductive layer 135 and a silicon substrate 130. The conductive layer 135 can include titanium (Ti) or nickel (Ni) layer. The substrate 130 may be an n-type silicon (100) flat wafer (3-8 $\Omega$-cm) or oxidized (30-50 nm $SiO_2$) p-type silicon (100) flat wafers (5-10 $\Omega$-cm). The thickness of this conductive metal film 135 can be controlled in the range of 100 Å-1,000 Å to provide adhesion to a noble metal layer that will be subsequently deposited. The noble metal layer can include Ag or Au. The thickness of the metal layer 135 is also optimized for applying an electric bias to the sensing surface for trace chemical detection and further for applying a lower temperature to the sensing surface to enhance sensitivity of trace chemical detection.

Figure 7D:
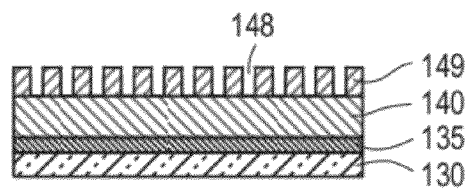
Figure 7B:
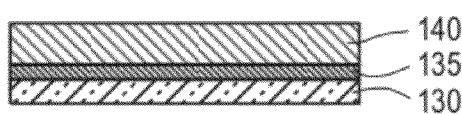

In FIG. 7B, a noble metal layer 140 is deposited on top of the conductive layer 135. The noble metal layer 140 can include silver and have a thickness of 10-200 nm. In FIG. 7C, a second metal layer 145, e.g., an aluminum layer with a purity of 99.999% with a thickness in the range of 1.0-10.0 micrometers, is deposited on top of the noble metal layer 140. Then an anneal operation is performed on the second metal layer 145 at 400° C.-500° C. in a $N_2$ purged furnace for 2-5 hours to recrystallize the Al film.

Shown in FIG. 7D, an anodization process is carried out to produce a porous structure in a form of porous aluminum oxide. A top view is shown in FIG. 7E where the porous structure is formed with naturally self-assembled hexagon-shaped nano pore-array that includes a plurality of pores 148 surrounded by hexagon-shaped pore wall 149. After removing top anodized layer by a wet chemical process, a second anodization process is carried out to consume all Aluminum material above the noble metal layer 140. Then a wet etch process is performed to widen the pores 148. As that shown in FIG. 7F, as the wet etch process proceeds, the pores 148 are widened and the walls 149 surrounding the pore become thinner. The etch process can be controlled to either form a plurality of nano-holes 148 surrounded by wall 149 or the pores 148 can be widen such that the pores 148 tangentially touch each other. The etching through the pores in the hexagonal array produce an array of quasi-triangle columns 149' (e.g. as an example of nano-rods compatible with the Raman sensor substrate 14 in FIG. 1).

Figure 7G:
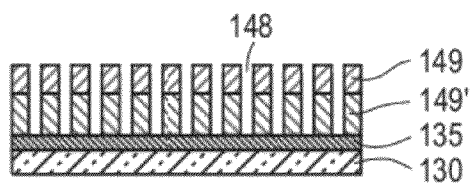
FIG. 7G is a cross-sectional view along line AA in FIG. 7E.
Figure 7C:
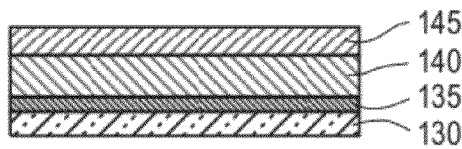
Figure 7E:
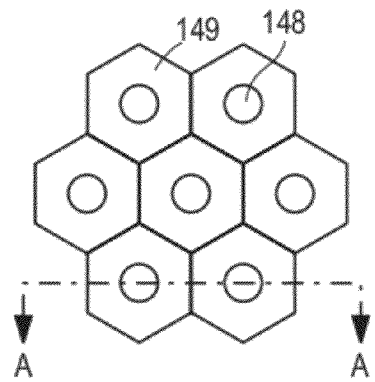
FIGS. 7E and 7F are top views of the nano structure of FIG. 7D.
Figure 7F:
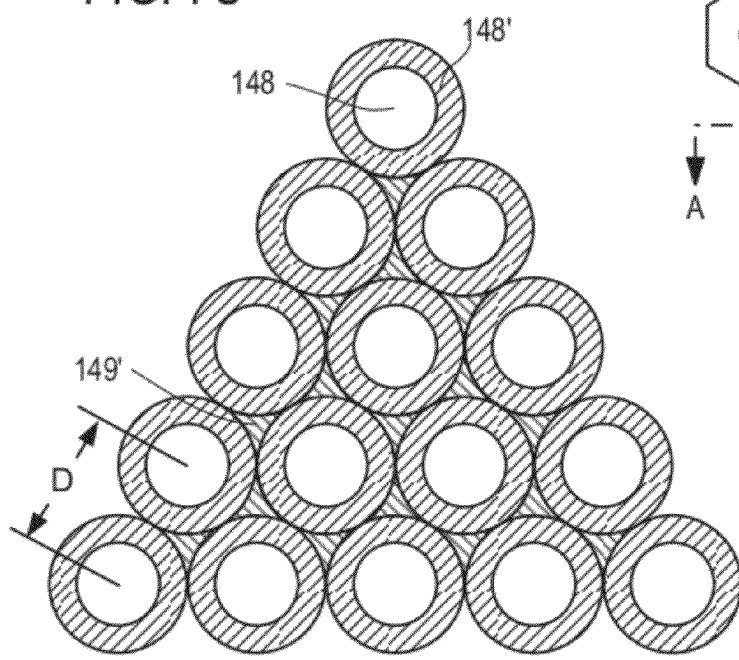

In FIGS. 7F and 7G, the noble metal layer 140 is etched down and the pores 148 are extended downward to reach the conductive titanium layer 135. The advantages of this method over the embodiment shown in FIGS. 1 to 6 as that discussed above are i) better film adhesion between the Ti layer 135 and the Ag layer 140, ii) shorter distance between adjacent nano holes, i.e., D as shown in FIG. 7F, with about 40% reduction comparing to $D_B$ if all other process conditions are the same, iii) the height of the nano rods 149' can be well-controlled by Ag PVD within ±2% in film thickness variation through the whole wafer containing at least several hundred or even several thousand devices.

According to above descriptions, the self-assembled nano sensing surface is formed that the Ag, Au or Cu triangle nano-rod array 149' or hexagonal nano-hole array 148' wherein each Ag, Au or Cu nano-rod or nano-hole array are spatially isolated from each other.

The nano-rod array dimension size can be well controlled by processes mentioned above. Specifically, the array dimension and size are well controlled within the ranges as set forth below:
 1) Ti film thickness: 10-1000 nm
 2) Nano rod diameter, d: 5-300 nm
 3) Nano rod inter-particle distance, D: 10-1000 nm
 4) Nano rod height, H: 10-1000 nm On the other hand, the nano-hole array dimension and size can be well controlled by processes mentioned above. Specifically:
 1) Ti film thickness: 10-1000 nm
 2) Nano hole diameter, d: 5-300 nm
 3) Nano hole inter-hole distance, D: 10-1000 nm
 4) Nano hole depth: 10-1000 nm In some embodiments, the Raman sensor substrate or test reagent 14 can include nano surface structures prepared by coating the surface of the sensor by a solution of a colloidal suspension of nano particles. After the solution is transferred to the surface, the solution can be evaporated to leave the nano particles on the surface. The nano particles have at least in one dimension with a size smaller than 1,000 nm. The nano particles are configured to adsorb the molecules of the substance to be tested.

In some embodiments, the Raman sensor substrate or test reagent 14 can include, for example, a sol gel containing nano particles. The nano particles have at least in one dimension with a size smaller than 1,000 nm. The nano particles are configured to adsorb the molecules of the substance to be tested.

In some embodiments, the sample solution containing the substance to be detected can be introduced with nano particles. The nano particles can adsorb the molecules of the substance to be tested. A laser beam is directed into an optically transparent sample container, such as test tube, cuvette, etc. An optical module collect scattered signal then transfer the signal to analyzer. The nano particles have at least one dimension smaller than 1,000 nm. The surfaces of the nano particles can greatly enhance Raman scattering signals from the molecules adsorbed on or in the vicinity of the nano particles. The substances to be detected in the sample solution can include chemical, biological, and medical substances.

Figure 3:
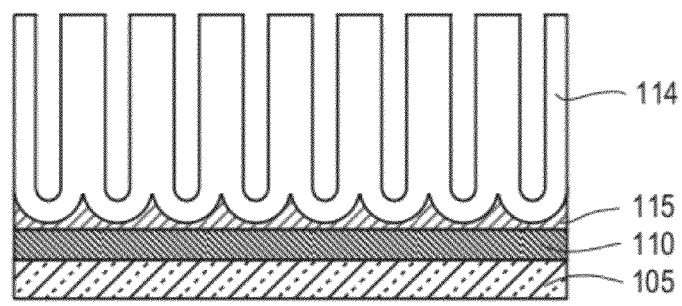
FIG. 3 is a cross-sectional view of the nano-structured surface after chemical etching or chemical mechanical polishing.
Figure 8:
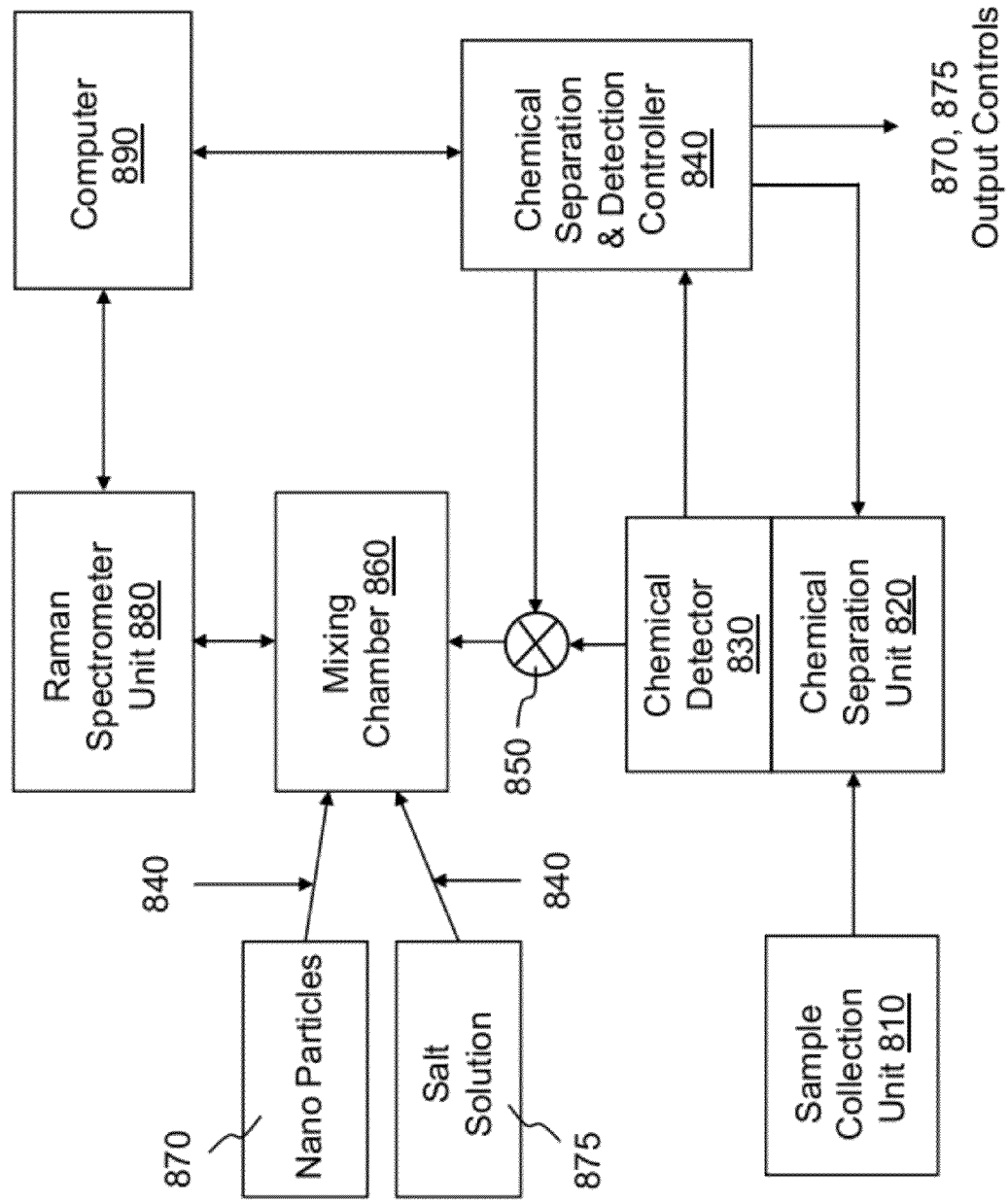
FIG. 8 is a system block diagram of another integrated Raman scattering chemical separation device in accordance to present invention.
Figure 9:
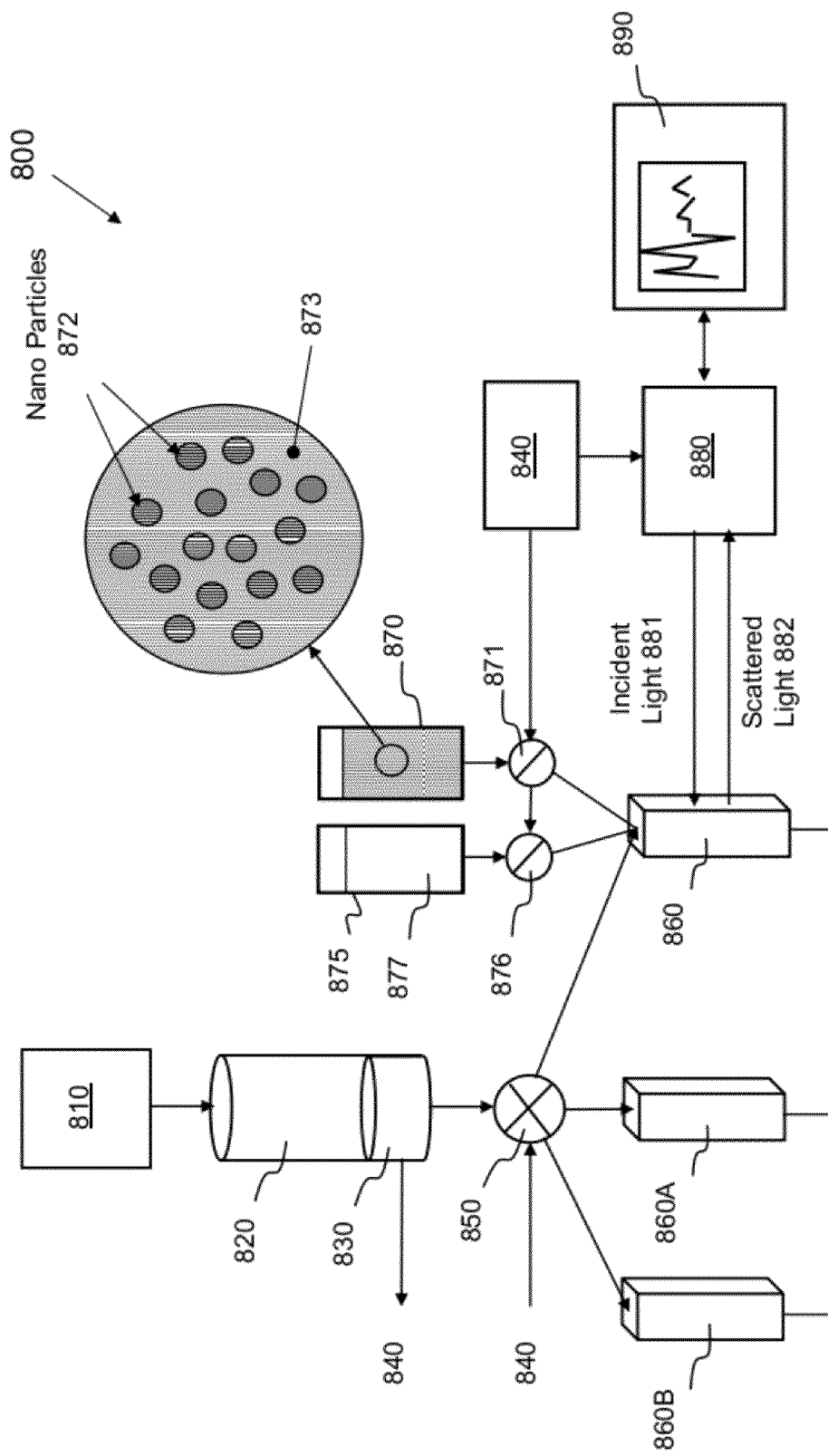
FIG. 9 is a schematic diagram of the integrated Raman scattering chemical separation device in FIG. 8.

Referring to FIGS. 8 and 9, an integrated Raman scattering chemical separation device 800 includes a sample collection unit 810, a chemical separation unit 820 configured to separate substances in a sample solution, a chemical detector 830, a chemical separation & detection controller 840, a multi-channel vale 850, a one or more mixing chambers 860, 860A, 860B, a container 870 for a solution containing nano particles 872, a container 875 for a salt solution 877, and valves 871, 876 respectfully for controlling the releases of the nano particle and the salt solutions into one of the mixing chambers 860, 860A, 860B. The integrated Raman scattering chemical separation device 800 also includes a Raman spectrometer unit 880 configured to obtain Raman signals from substances in the sample solution and a computer 890 for analyzing the Raman spectra. The above cited components in the integrated Raman scattering chemical separation device 800 can be integrated and contained in or held by a single device body similar to the device bodies 21, 31 (FIGS. 2 and 3). The device body can include a rigid chassis, a chamber, a rigid fixture or frame that can define an enclosure. Similar to what shown in FIGS. 2 and 3, the integrated Raman scattering chemical separation device 800 can be made in compact device body that is easily portable.

The sample collection unit 810 can collect samples from a gas, a liquid, a solid, or an aerosol. A sample may contain trace chemical that is to be detected and identified by the integrated Raman scattering chemical separation device 800. The sample is prepared in a sample solution. The sample collection unit 810 can perform preliminary filtering to remove solid particles, physical debris, and unwanted chemical components and impurities, etc. For example, to analyze an environmental sample obtained from a river, sands, debris, leaves, and plants can be removed by the sample collection unit 810.

The chemical separation unit 820 is configured to separate the substances contained in the sample under the control of the chemical separation & detection controller 840. The chemical separation & detection controller 840 can control the pressure and the temperature of the fluid (a liquid or a gas) or the aerosol in the chemical separation unit 820 to produce more distinct separation of the chemicals. The chemical separation unit 820 can be based chemical separation methods (LC, HPLC, GC, or IC). In liquid chromatography (LC) and high performance liquid chromatography (HPLC), the sample is prepared in solutions and carried out—by mobile phase into columns. Different chemical compositions are separated through their chemical properties by the different times, called retention time, which the chemicals take to flow out of the columns. In some embodiments, the chemical separation and detection controller 840 can control pressure or temperature of the sample solution in the chemical separation unit 820 to make sample solution mobile in the column for a period of retention time.

Figure 10:
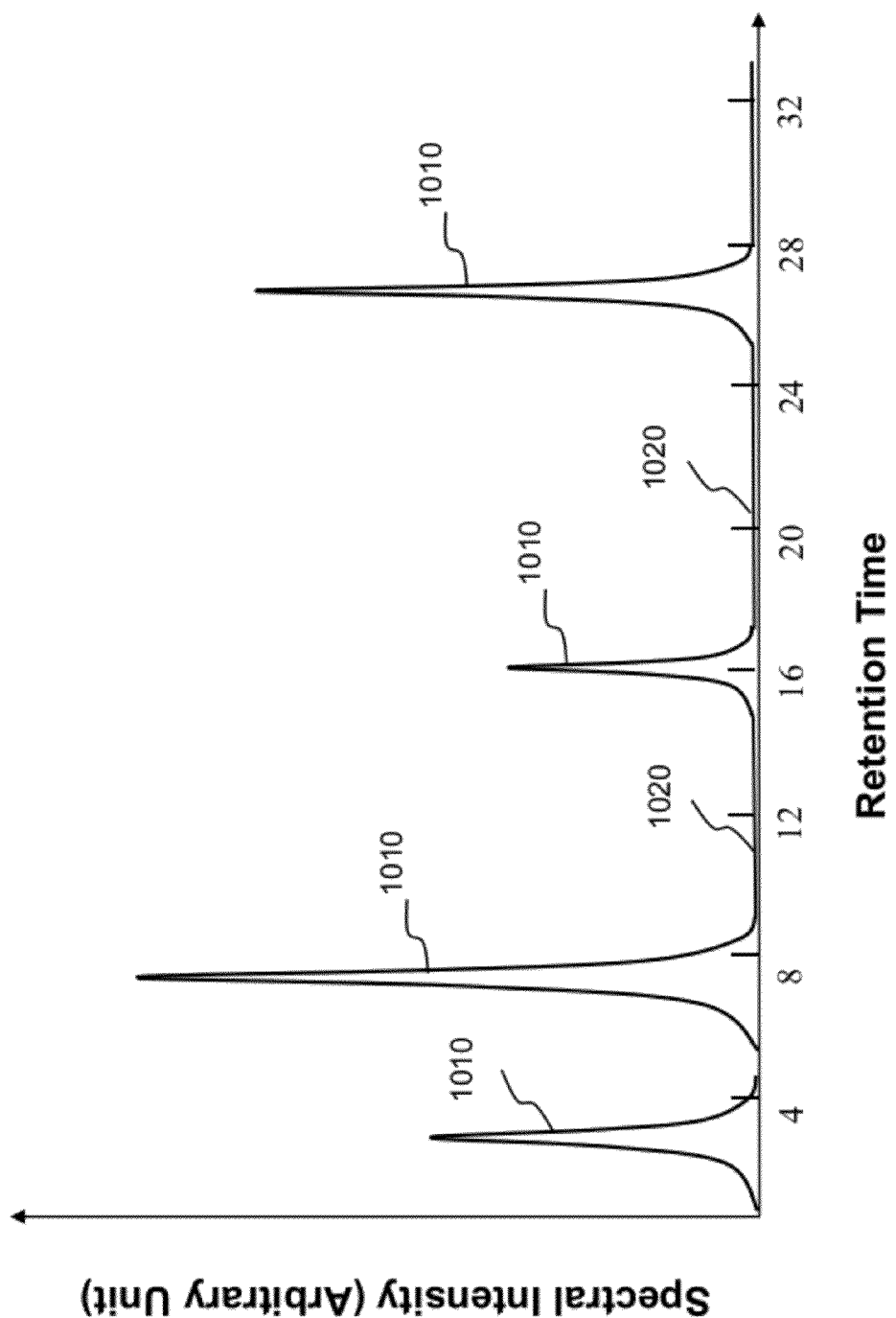
FIG. 10 shows an exemplified spectral signal profile for substances separated by an LC or HPLC.

The chemical detector 830 can detect the different substances as they flow out of the chemical separation unit 820 at different times. For example, the chemical detector 830 can include a UV spectrometer that detects spectral peaks of different chemical substances as shown in FIG. 10. The spectral peaks 1010 of the different chemicals are temporarily separated by a low spectral background 1020 of the mobile phase of the solution. Each time a spectral peak is detected, the chemical detector 830 sends a detection signal to the chemical separation & detection controller 840.

In response to the detection signal, after a time lag for the sample solution to flow from the chemical detector 830, the chemical separation & detection controller 840 switches the multi-channel valve 850 to direct the sample solution from the chemical separation unit 820 to one of the mixing chambers 860, 860A, 860B. For example, the sample solution can be directed to the mixing chamber 860 (shown in FIG. 9). The valve 871 is in fluidic communication with the container 870 and the mixing chamber 860. The valve 876 is in fluidic communication with the container 875 and the mixing chamber 860. The chemical separation & detection controller 840 controls the valves 871, 876 to respectively release the nano particle solution 873 and the salt solution 877 to mix with the sample solution in the mixing chamber 860. The molecules of the substance to be detected are absorbed on nano particles 872 (FIG. 11A).

When a substance represented by a spectral peak 1010 (FIG. 10) has passed, the multi-channel valve 850 can be switched to direct the mobile phase of the sample solution (the clear sample solution corresponding to the spectral background between spectral peaks in FIG. 10) to an effluent exit (not shown). Moreover, the mobile phase solution can be used to clean a substance in the mixing chambers 860, 860A, 860B and columns after each spectral measurement. The mixing chambers 860, 860A, 860B each can include an effluent exit to discard sample solutions to a disposal 865 after each spectral measurement.

It should be noted that other mixing chambers 860A, 860B each can also be in valve controlled fluidic communications (not shown in FIG. 9) with the containers 870, 875 to receive nano particle and salt solution to mix with the sample solutions once they arrive at the respective mixing chambers 860A, 860B.

Figure 11A:
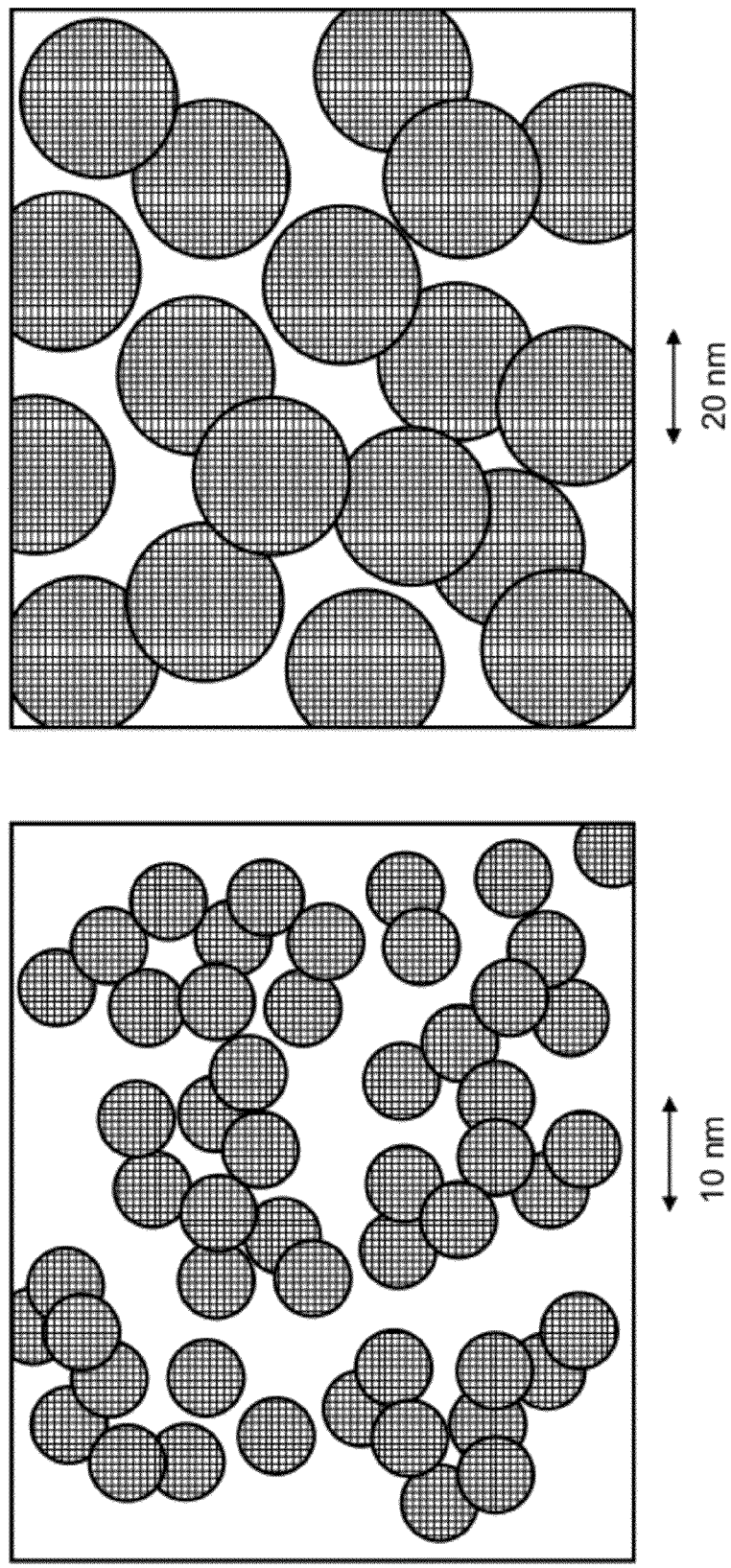
FIG. 11A is an exemplified scanning electron micrograph of the nano particles suitable for the integrated Raman scattering chemical separation device in FIG. 8.
Figure 11B:
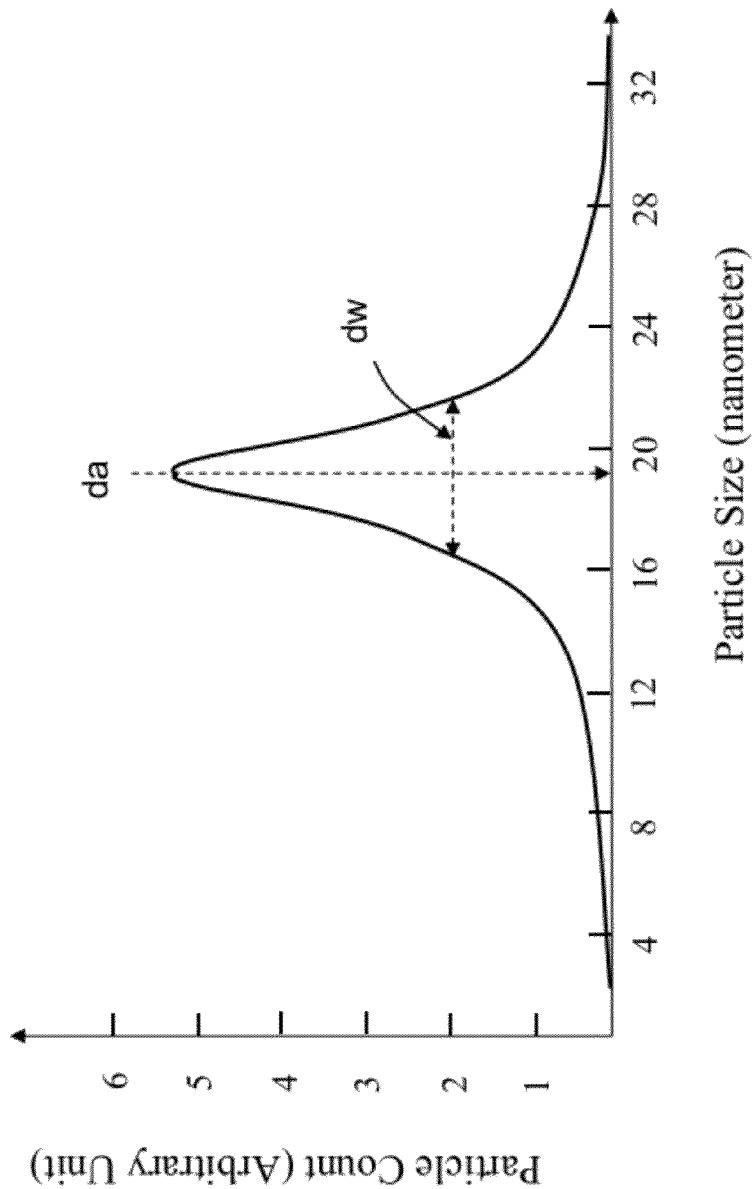
FIG. 11B is an exemplified size distribution of the nano particles suitable for the grated Raman scattering chemical separation device in FIG. 8.

The nano particles 872, as shown in FIGS. 9 and 11A, can exist in round or irregular shapes. The nano particles can be individually separated and have also group in clusters in a solution 873. The nano particles 872 can have a size distribution, as shown in FIG. 11B, which is characterized by an average particle dimension da and a distribution width dw for the particle size distribution. The average particle dimension da can range from about 1 nm to about 10,000 nm, or from 2 nm to 500 nm. The ratio dw/da can range from about 0.01 to about 3, which defines a quite monodispersed distribution to a polydispersed particle distribution. The ratio dw/da can often range from about 0.03 to about 1.

The nano particles 872 can be made of a metallic material such as Al, Ag, Au, Cu, Fe, Co, Ni, Cr, Zn, Sn, Pd, Pt, and their alloys, oxide materials such as titanium oxide, silicon oxide, zinc oxide, etc, silicon, and polymeric materials. The nano particles 872 can be formed by a single-phase material, or by two or more phase materials in core-shell structures. The nano particles 872 can be charged in the sample solution to assist the separation between the nano particles 872 and the formation of a colloidal suspension. The nano particles 872 can also include polymers tethered to the particle surfaces to help repel each other in the sample solution.

In another aspect of the present disclosure, the nano particles 872 can be made of a magnetic or ferromagnetic material such as Iron (Fe), Cobalt (Co), and Nickel (Ni), or Fe-, Co-, Ni-containing compounds, such as alloy or oxide of Fe, Co, Ni. The nano particles 872 can be formed by a single-phase material, or by two or more phase materials in core-shell structures. A capacitor or electromagnet (not shown) can enhance the Raman spectral signal by applying an electrical field, a magnetic field, or an electro-magnetic field to the sample solution mixing chambers 860, 860A, 860B. The electrical field, the magnetic field, or the electro-magnetic field can be static or alternating.

In another aspect of the present disclosure, the solution 873 can carry a mixture of nano particles 872 of different material compositions. For example, the nano particles 872 can include a mixture of silicon nano or micro-particles and metallic nano particles, or a mixture of silicon nano or micro-particles and polymeric nano particles, or a mixture of silicon nano or micro-particles, metallic nano particle, metallic oxide nano particles, and polymeric nano particles. Raman signal intensity can be enhanced by mixture compositions.

In some embodiments, the nano particles 872 can include carbon nano tubes. The diameters of the carbon nano tubes are smaller than 1,000 nm. For example, the diameters of the carbon nano tubes can be from 0.3 nm to 100 nm. Their lengths can be from 5 nm to multiple millimeters. The length-to-diameter ratio of the carbon nano tubes can be as high as 50 million. The carbon nano tubes can have single-walls or multiple walls. The carbon nano tubes can be in the form of Fullerite, a torus, nanobuds, and nanoflowers.

The salt solution 877 is also prepared to enhance the light scattering intensity from the nano particles 872. The salt solution 877 can include ions and especially multi-valence ions that the inventors found to significantly enhance signal intensities of Raman scattering signals from the trace chemicals. Examples of ions in the salt solution 877 include $Na^+$, $K^+$, $Li^+$, $Ca^{++}$, $Ba^{++}$, $Sr^{++}$, $Mg^{++}$, $Mn^{++}$, $Al^{+++}$, $Zn^{++}$, $Sn^{++}$, $Sn^{++++}$, $F^-$, $Cl^-$, $Br^-$, and $I^-$, and so on. The ions can have mono charge or preferably double or high charges, positive or negative charges. The salt solution 877 can contain ionic compounds, including but not limited to LiF, NaF, NaCl, KCl, KI, etc. The ionic concentration of the sample solution can be in a range from 0.1 mM to saturated level after it is introduced with the salt solution 877.

The Raman spectrometer unit 880 includes a light source (e.g. a laser device) and a Raman spectrometer. The mixing chambers 860, 860A, 860B include a flat transparent wall or window to receive an incident light 881 from the light source and allow scattered light 882 to exit and be collected by the Raman spectrometer in the Raman spectrometer unit 880. The mixing chambers 860, 860A, 860B can be implemented as flow-through optical cells. The light source in the Raman spectrometer unit 880 can receive timing signals about the time when the multi-channel valve 850 is witched toward the mixing chamber 860 and the times when the nano particle solution 873 and the salt solution 877 are respectively released by the valves 871, 876. The light source can emit the incident light 881 at the time the sample solution is mixed with the nano particle solution 873 and the salt solution 877 in the mixing chamber 860. Raman spectrum is obtained by the computer 890 from the scattered light 882. Trace chemicals can be identified using spectral signatures as described above.

In some embodiments, referring to FIG. 9, the mixing chambers 860, 860A, 860B provide parallel substance detection channels for different substances flowing out sequentially from the chemical separation unit 820. The substances represented by sequential spectral peaks 1010 (in FIG. 10) can be directed to different mixing chambers 860, 860A, 860B (FIG. 9) to allow each substance to have sufficient time for signal collection. This feature of multiplexing detection channels is particularly beneficial for detecting and identifying chemicals that have adjacent spectral peaks.

Figure 12:
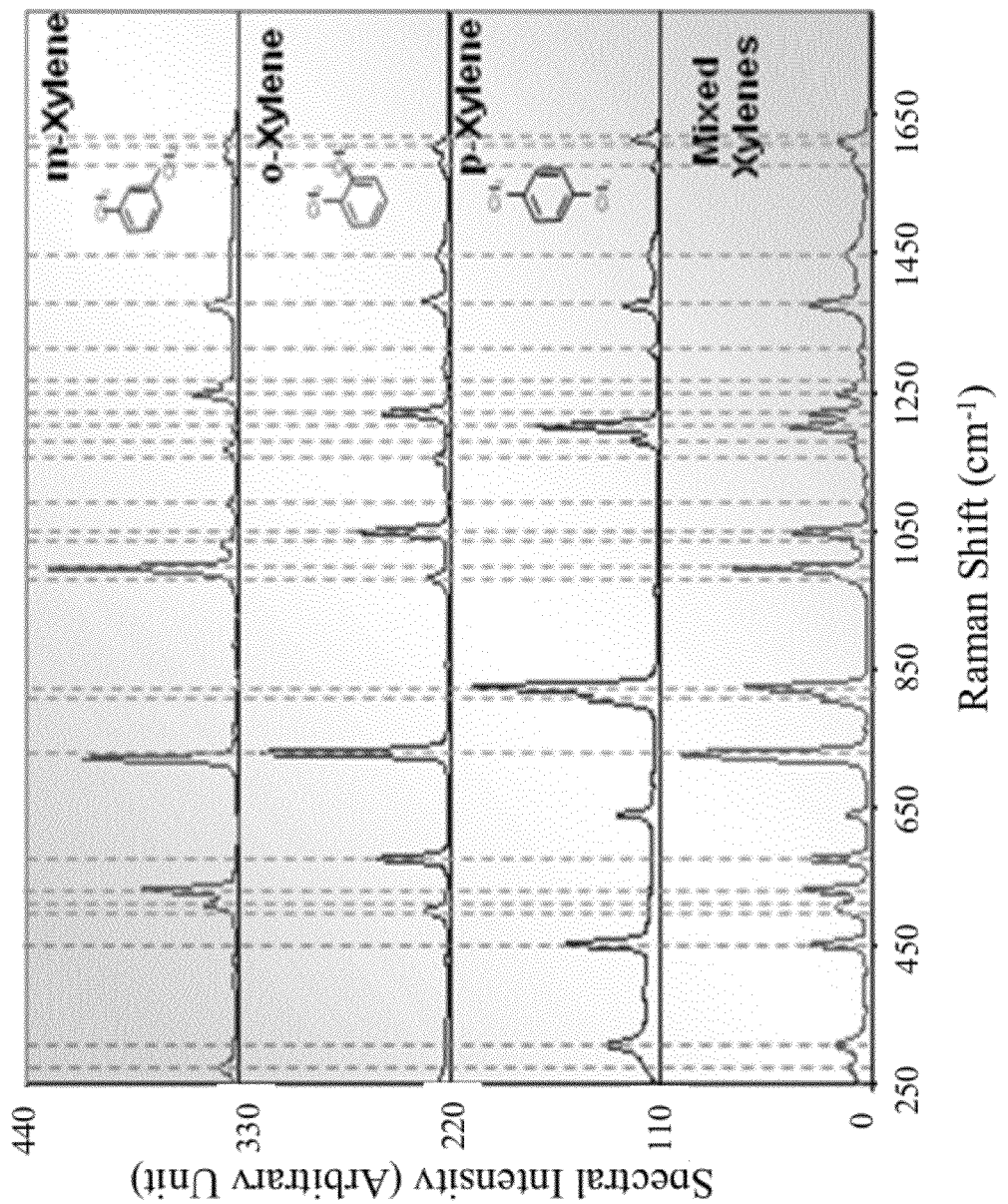
FIG. 12 shows Raman spectral data of a few exemplified substances.

FIG. 12 shows Raman spectral data for xylene isomers that can be obtained by the integrated Raman scattering chemical separation device 800 (FIG. 8). The xylene isomers include m-xylene, o-xylene, p-xylene, and a mixture of different types of xylenes. Each substance is characterized by different sets of spectral peaks which can be used as signatures for identifying the substances.

Figure 13:
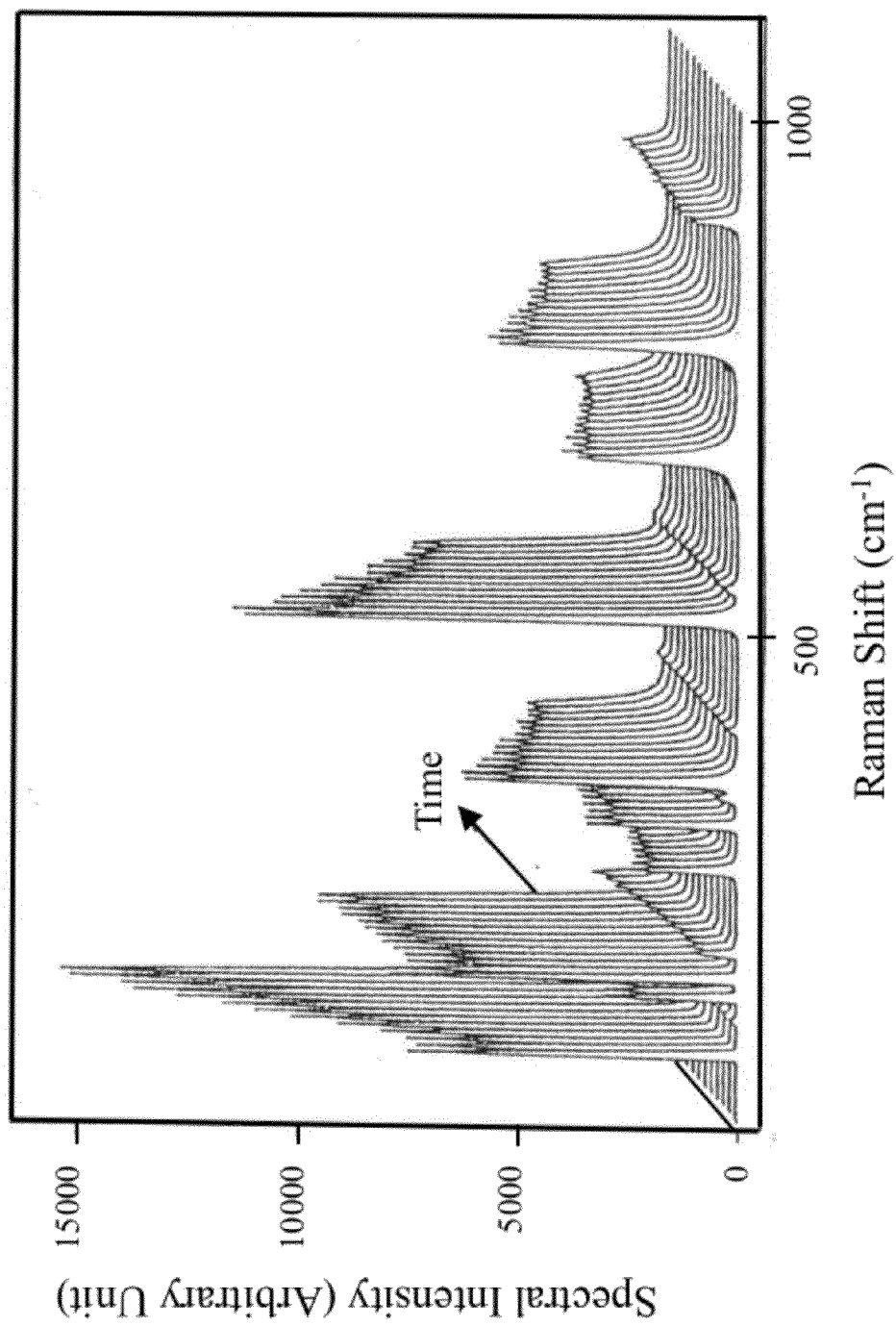
FIG. 13 is a plot of exemplified Raman spectral data obtained by the integrated Raman scattering chemical separation device in FIG. 8.

The integrated Raman scattering chemical separation device 800 (FIG. 8) can provide rich spectral data for analyzing a group of substances in a sample solution in an efficient manner. Referring to FIG. 13, the computer 890 (FIGS. 8 and 9) can collect large amount of spectral data in one sample run of LC or HPLC. For Raman scattering based substance detection, for each substance represented by a spectral peak 1010 shown in FIG. 10, a Raman spectral curve is obtained by plotting the spectral intensity (the vertical axis) versus Raman shift (horizontal axis). As different substances move out of the chemical separation unit 820 over a period of retention time, Raman spectral curves can be obtained for different substances in the same sample solution. Some Raman spectral peaks will appear or disappear for different substances. The strengths of the Raman spectral peaks also vary for different substances or for different substance concentrations. The spectral peaks and their Raman shift position, as well as the shapes and relative intensities of the peaks, can be used to effectively identify chemical names and their trace amount of substances in a sample solution in a sequential workflow (one sample run) and using an integrated measurement device.

Although specific embodiments of the present invention have been illustrated in the accompanying drawings and described in the foregoing detailed description, it will be understood that the invention is not limited to the particular embodiments described herein, but is capable of numerous rearrangements, modifications, and substitutions without departing from the spirit of the disclosed invention. For example, the disclosed system is compatible with different computer devices that can access the website, and different layouts and different forms of web user interfaces on computer devices.

What is claimed is:

1. An integrated chemical separation device, comprising:
   a single device body;
   a chemical separation unit mounted to the single device body and configured to separate a chemical from a fluid or an aerosol;
   a Raman sensor mounted to or in the single device body and configured to receive the chemical from the chemical separation unit, wherein the Raman sensor includes a plurality of nano rods, nano holes, or nano particles configured to adsorb molecules of the chemical from the fluid or the aerosol; and
   a Raman scattering spectrometer unit mounted to the single device body and configured to emit a laser beam to illuminate the molecules adsorbed on surfaces of the nano rods, nano holes, or nano particles to obtain Raman spectra from the plurality of substances.

2. The integrated chemical separation device of claim 1, wherein the chemical separation unit comprises a liquid chromatography (LC) column or a high performance liquid chromatography (HPLC) column.

3. The integrated chemical separation device of claim 1, wherein the chemical separation and detection controller is configured to control temperature or pressure of the fluid in the chemical separation unit.

4. The integrated chemical separation device of claim 1, wherein the Raman scattering spectrometer unit comprises:
 a laser source configured to emit the laser beam to illuminate the molecules adsorbed on the nano rods, the nano holes, or the nano particles; and
 a Raman spectrometer configured to produce a Raman spectrum in response to scattered light from the molecules adsorbed on the surfaces of the nano rods, the nano holes, or the nano particles.

5. The integrated chemical separation device of claim 1, wherein the nano particles have average diameters ranging from 2 nm to 500 nm.

6. The integrated chemical separation device of claim 1, wherein the nano particles have a size distribution characterized by an average diameter da and a distribution width dw, wherein the ratio dw/da is between about 0.01 and about 3.

7. The integrated chemical separation device of claim 1, wherein the nano particles comprise a material selected from a group consisting of a metal, a metal alloy, an oxide material, silicon, a polymeric material, a magnetic or ferromagnetic material, carbon nano tubes, or a combination thereof.

8. The integrated chemical separation device of claim 1, wherein the nano particles comprise Al, Ag, Au, Cu, Fe, Co, Ni, Cr, Zn, Sn, Pd, Pt, C, or Si, or oxide thereof, or a combination thereof.

9. The integrated chemical separation device of claim 1, wherein the nano particles are formed in a core-shell structure by two or more materials.

10. The integrated chemical separation device of claim 1, further comprising:
 a computer configured to identify the plurality of substances from the light scattered from the molecules adsorbed on the nano particles.

11. The integrated chemical separation device of claim 1, wherein the fluid comprises a plurality of substances comprising the chemical, wherein the chemical separation unit is configured to sequentially output of the plurality of substances, wherein the Raman sensor comprises one or more mixing chambers configured to receive the plurality of substances at different times, the integrated chemical separation device further comprising:
 a chemical separation and detection controller; and
 a multi-channel valve configured to sequentially direct the plurality of substances to the one or more mixing chambers under the control of the chemical separation and detection controller, wherein the chemical separation and detection controller is configured to introduce the nano particles in the one or more mixing chambers to allow each of the plurality of substances to be adsorbed on the nano particles.

12. The integrated chemical separation device of claim 11, further comprising:
 a chemical detector coupled to the output of the chemical separation unit, wherein the chemical detector is configured to detect the plurality of substances as each of the plurality of substances exits the chemical separation unit and to send a detection signal to the chemical separation and detection controller, wherein the chemical separation and detection controller is configured to switch the multi-channel valve to direct one of the plurality of substances to one of the one or more mixing chambers.

13. The integrated chemical separation device of claim 11, wherein the chemical separation and detection controller is configured to control the multi-channel valve to direct adjacent substances of the plurality of substances to different ones of the one or more mixing chambers.

14. The integrated chemical separation device of claim 11, wherein the chemical separation and detection controller is configured to introduce a salt solution in the one or more mixing chambers to enhance intensities of the Raman spectra.

15. The integrated chemical separation device of claim 14, wherein the salt solution comprises multi-valence ions.

16. The integrated chemical separation device of claim 14, wherein the salt solution comprises $Na^+$, $K^+$, $Li^+$, $Ca^{++}$, $Ba^{++}$, $Sr^{++}$, $Mg^{++}$, $Mn^{++}$, $Al^{+++}$, $Zn^{++}$, $Sn^{++}$, $Sn^{++++}$, $F^-$, $Cl^-$, $Br^-$, or $I^-$.

17. The integrated chemical separation device of claim 14, wherein after mixing with the salt solution, the one or more mixing chambers have an ionic concentration from about 0.1 mM to a saturated level.

18. The integrated chemical separation device of claim 11, wherein the Raman sensor comprises a first container configured to hold a nano particle solution comprising the nano particles, the integrated chemical separation device further comprising:
 a first valve in fluidic communication with the first container and one of the one or more mixing chambers, wherein the chemical separation and detection controller is configured to control opening and closing of the first valve to control releases of the nano particles into the one or more mixing chambers.

19. The integrated chemical separation device of claim 18, wherein the Raman sensor comprises a second solution container configured to a salt solution, the integrated chemical separation device further comprising:
 a second valve in fluidic communication with the second container and the one of the one or more mixing chambers, wherein the chemical separation and detection controller is configured to control opening and closing of the second valve to control releases of the salt solution into the one or more mixing chambers.

20. The integrated chemical separation device of claim 11, wherein the one or more mixing chambers each comprises a transparent wall or window to allow transmission of the laser beam and the scattered light.

* * * * *